United States Patent
Czaja et al.

(10) Patent No.: US 12,366,496 B2
(45) Date of Patent: Jul. 22, 2025

(54) METHODS FOR CALIBRATING A MOTION AND GROUND REACTION FORCE ANALYSIS SYSTEM

(71) Applicant: Motion Metrics Limited, London (GB)

(72) Inventors: Stanislaw Czaja, Cardiff, CA (US); Lora O'Leary, Cardiff, CA (US); James Anthony Salter, London (GB); Harry Charles Bickerton, London (GB); Sam Jana Van Den Brink, Innsbruck (AT)

(73) Assignee: Motion Metrics Limited, London (GB)

( * ) Notice: Subject to any disclaimer, the term of this patent is extended or adjusted under 35 U.S.C. 154(b) by 35 days.

(21) Appl. No.: 18/494,923

(22) Filed: Oct. 26, 2023

(65) Prior Publication Data
US 2024/0060842 A1  Feb. 22, 2024

Related U.S. Application Data

(63) Continuation-in-part of application No. 17/204,817, filed on Mar. 17, 2021, now Pat. No. 11,832,931, (Continued)

(51) Int. Cl.
| | |
|---|---|
| *G01L 25/00* | (2006.01) |
| *A61B 5/00* | (2006.01) |
| *A61B 5/103* | (2006.01) |

(52) U.S. Cl.
CPC ............ *G01L 25/00* (2013.01); *A61B 5/1036* (2013.01); *A61B 5/6807* (2013.01); *A61B 2560/0223* (2013.01); *A61B 2560/0257* (2013.01); *A61B 2562/0219* (2013.01); *A61B 2562/0247* (2013.01); *A61B 2562/028* (2013.01); *A61B 2562/046* (2013.01)

(58) Field of Classification Search
CPC ..... G01L 25/00; A61B 5/1036; A61B 5/6807; A61B 2560/0223; A61B 2560/0257; (Continued)

(56) References Cited

U.S. PATENT DOCUMENTS

| | | |
|---|---|---|
| 6,498,994 B2 | 12/2002 | Vock et al. |
| 9,486,669 B2 | 11/2016 | Niegowski et al. |

(Continued)

OTHER PUBLICATIONS

Andriamandroso A.L.H, Lebeau F, Beckers Y, Froidmont E, Dufrasne I, Heinesch B, Dumortier P, Blanchy G, Blaise Y, Bindelle J. 2017. Development of an open-source algorithm based on inertial measurement units (IMU) of a smartphone to detect cattle grass intake and ruminating behaviors. Computers and Electronics in Agriculture, 139, 126-137: https://doi.org/10.1016/j.compag.2017.05.020.

(Continued)

*Primary Examiner* — Timothy A Musselman
(74) *Attorney, Agent, or Firm* — Intrinsic Law Corp.

(57) ABSTRACT

A method of calibration of a system designed for analysis of ground reaction forces of a user's feet, wherein the system comprises a left and right footwear each with a plurality of force sensors. The method includes (a) obtaining respective data measurements from each force sensor over a time period while the user's feet are in the left and right footwear; (b) determining a respective statistic of the respective data measurements for each force sensor over the time period; and (c) storing the respective statistic as a respective calibration offset for a respective force sensor. The respective statistic may comprise a minimum, a maximum, an average, a median, a percentile, and/or a statistical model of the respective data measurements.

21 Claims, 22 Drawing Sheets

Related U.S. Application Data which is a continuation-in-part of application No. 15/953,439, filed on Apr. 14, 2018, now abandoned, which is a continuation-in-part of application No. 14/747,179, filed on Jun. 23, 2015, now Pat. No. 9,968,840.

(58) Field of Classification Search
CPC .... A61B 2562/0257; A61B 2562/0219; A61B 2562/0247; A61B 2562/028; A61B 2562/046; A61B 5/1038

See application file for complete search history.

(56) References Cited

U.S. PATENT DOCUMENTS

| | | | |
|---|---|---|---|
| 10,034,622 B1 * | 7/2018 | Mahmoud | ............... A43B 3/34 |
| 2010/0063778 A1 | 3/2010 | Schrock et al. | |
| 2012/0253234 A1 | 10/2012 | Yang et al. | |
| 2013/0023798 A1 | 1/2013 | Greene et al. | |
| 2013/0191034 A1 | 7/2013 | Weast et al. | |
| 2014/0182170 A1 | 7/2014 | Wawrousek et al. | |
| 2016/0321947 A1 | 11/2016 | Toronto et al. | |
| 2016/0335913 A1 | 11/2016 | Grant et al. | |
| 2017/0265584 A1 | 9/2017 | Walker et al. | |
| 2017/0287212 A1 | 10/2017 | Tran et al. | |
| 2017/0332946 A1 | 11/2017 | Kikkeri | |
| 2018/0054663 A1 | 2/2018 | Markison et al. | |
| 2018/0279915 A1 | 10/2018 | Huang et al. | |

OTHER PUBLICATIONS

Earl, Bill. "Calibrating Sensors" Adafruit Learning System, Last Updated Aug. 29, 2023, learn.adafruit.com/calibrating-sensors?view=all.

"How Do You Calibrate an Accelerometer?" Technical Information Library, Mar. 18, 2020, www.vernier.com/til/418.

* cited by examiner

METHODS FOR CALIBRATING A MOTION AND GROUND REACTION FORCE ANALYSIS SYSTEM

CROSS-REFERENCE TO RELATED APPLICATIONS

This application is a continuation-in-part of U.S. application Ser. No. 17/204,817, filed on Mar. 17, 2021, titled "Methods for Calibrating a Motion and Ground Reaction Force Analysis System," which is a continuation-in-part of U.S. application Ser. No. 15/953,439, filed on Apr. 14, 2018, titled "Method for Calibrating Local Coordinates and Force Reference of Motion and Ground Reaction Force Analysis System," which is a continuation-in-part of U.S. application Ser. No. 14/747,179, now U.S. Pat. No. 9,968,840, filed on Jun. 23, 2015, titled "Method and Apparatus to Provide Haptic and Visual Feedback of Skier Foot Motion and Forces Transmitted to the Ski Boots," all hereby incorporated by reference in their entirety as though fully and completely set forth herein.

TECHNICAL FIELD

The present invention relates to the field of visualization of motion and weight distribution inside the ski (or skate) boot for the purpose of monitoring forces projected through the foot to the ski and snow to aid in training and performance evaluation. A gyroscope, accelerometer, magnetometer, pressure and force sensors are embedded into the sole of the ski boot (or ice skating-boot), providing measurement of foot rotational and lateral motions in 10-degree of freedom. Furthermore, one or more actuators are embedded in the ski boot insole, providing haptic feedback to the skier foot. The motion and weight distribution vectors are processed by the micro-controller embedded in the boot sole, and the resulting motion matrices are transmitted to the user smart-phone using Bluetooth, or other suitable short range radio interface. Alternatively, the data from motion sensors may be transmitted to the user smart-phone for processing of motion fusion matrices. The results are synchronized to GPS time and coordinates, then after applying appropriate filtering, the results are transmitted to one or more actuators embedded in the boot insole, providing haptic feedback to the user, indicating the timing and the direction of force distribution between feet and inside each ski boot used to execute turn. Results are also transmitted to the remote location ("cloud service") for further processing using smart-phone cellular radio interface. Said processing includes presenting of the foot motion and force distribution in a form of animation and superimposing said data on the 3D maps obtained from GPS coordinates. The post-processed visual and numeric data may then be received from the cloud server by the user smart-phone or by a remote computer terminal. Furthermore, if an accident (fall without recovery over certain period of time and warning cancellation), is detected, an SMS message informing of said accident is sent to the predefined recipients.

BACKGROUND

Currently monitoring of skier/skiing performance relies on few techniques, such as: skier feelings, instructor/coach observations, etc., and some empirical factors, such as: time measurements, post run video analysis, while the safety and comfort depends on decades old ski binding technology, incremental progress in materials and manufacturing technology. Some analytical methods for data collection during the development phase of the ski equipment are in use today, however, most of those techniques are not practical for everyday training of a professional or a recreational skier, as they require bulky equipment and require large team of highly skilled technicians to operate.

The comfort, safety and pleasure of skiing are highly dependent on the improvement of the user skills. While most beginners may relay initially on lessons and advise from a ski instructor and make initial progress, progress of most intermediate skiers is slow, painful and based on correction of errors, while progress of professionals is correlated directly to the quality and attention of the coach and the quality and duration of training. In the past, some innovation in recording the pressure points projected by the skier foot on the ski boot insoles were introduced in an attempt to analyze bio-mechanics and as an aid in training. However, those devices can only record distribution of pressure and require synchronization with real-time video of the run to provide meaningful information. And as real-time video synchronization is rarely available to the average skiing enthusiast, the benefit of such devices in training is very limited.

In recent years, the use of mobile devices and, in particular, smart-phones proliferated, all provided by the progress in electronics circuit integration. Today's smart-phone besides providing communication over cellular network is equipped with various input/output capabilities, such as wireless PAN (Personal Area Network), and provides significant computing resources. Such computing and communication resources may be integrated with a motion analyzer embedded into replaceable sole of a ski boot (or skate boot), to provide level and quality of feedback suitable for all—from beginners to professionals. A motion analyzer embedded in the ski boot (skate boot) sole communicating with the user smart-phone or a dedicated cellular interface modem, provides capability to visualize the run characteristic values. The run characteristic values may be stored in the "Internet cloud" for post-analysis or displayed in real-time in a remote location. Such system can be used as an aid in instruction, or as a tool in objective determination of athlete performance—i. e. to determine quality of performance by the free-style skier. Such system may operate using any of wireless technology such as: cdma2000, UMTS, WiMax, LTE. LTE-A, etc.

SUMMARY

This invention describes system allowing visualization of skier's (or ice-skater's) foot motion and distribution pressure points inside the ski boot while providing haptic feedback in a real time by embedding miniature micro-mechanical systems (MEMS) and electronics components into the inner sole of the ski boot. The system comprises of: 3-axis accelerometer, 3-axis gyroscope and a 3-axis magnetometer, to provide motion vectors in 9-degree of freedom. In addition, an atmospheric pressure sensor to provide measurement in changes of atmospheric pressure—to record vertical motion, and two or more force-pressure sensors—to record forces applied to the toe and heel of the boot, are added. Such system provides measurement of linear acceleration, rotational vectors and orientation (attitude) in three-dimensional space providing representation of motion. This motion and vectors are synchronized with GPS time and coordinates are sent to a remote location for processing and presentation in visual and numerical form. Such presentation may be used to understand the precise cause—in relation to time/position of the error made by the skier to aid in training and/or provide link to references explaining the nature of error and suggesting remedy. Furthermore, a haptic feedback actuator located under the user's big toe provides feedback (and advise) about changes in distribution of the forces inside each ski boot, which are necessary to execute the desired turn. This feedback is based on the analysis of the current phase of the turn, information about the user and equipment physical parameters and the knowledge of the points on the force of user feet, which must be applied to achieve smooth transition between different phases of the turn. Beside aiding in training, the visual presentation of the athlete's movement in 3D space and/or the topological information, may aid in providing objective assessment of the performance in such disciplines as: free-style skiing, ice skating, etc.

The motion processing system of the present invention comprises motion capture sub-system consisting of: a multi-axis accelerometer, gyroscope and magnetometer (compass), plus a barometric pressure and force sensors; a microprocessor; and a personal area network (PAN) radio interface to communicate motion vectors to the smart-phone based application. According to one embodiment of this invention, said motion sub-system is embedded in a replaceable sole of the ski boot inner-lining, while in another embodiment of this invention, the motion capture sub-system is directly embedded in the ski boot.

It is well known that ski or snowboard turns when moments are applied to the ski edge by skier's body through the forces applied to the skier's foot, and that the turning performance is determined by said forces and the reactions introduced by ski-snow contact. Understanding of skiing bio-mechanics allows determination of proper pressure distribution on the skier's foot in order to make the foot pronate to control the external forces that disturb equilibrium of balance. To establish balance platform, skier must place the center of pressure on the outside (of the turn) foot, and only in specific conditions during the turn. In the foot/ski boot system, the center of pressure (COP), lays at the point where the resulting force (FR) of interaction between the ski and snow acting on a skier at ski between the turns (flat phase of turn), pulls his center of mass (COM) downward towards the snow and is opposed by muscles preventing a fall. Said knowledge may be augmented with real-time tracking of ski boot motion and the distribution of pressure points inside the ski boot during difference phases of turn.

Analyzing motion, one may determine the current phase of the turn and knowing the skier and equipment physical parameters may predict (extrapolate) the desired rate of ski rotation, then provide haptic stimulus indicating time the COP must be transferred form one part of the foot to another part. Such system, comprising motion and pressure sensors embedded in the ski boots and a smart-phone based application may provide real-time feedback to the skier and visual post-run analysis does provide tool in training.

An aspect of the invention is directed to a method of calibration of a system designed for analysis of ground reaction forces of a user's feet, wherein the system comprises a left and right footwear each with a plurality of force sensors, the method comprising: (a) obtaining respective data measurements from each force sensor over a time period while the user's feet are in the left and right footwear; (b) determining a respective statistic of the respective data measurements for each force sensor over the time period; and (c) storing the respective statistic as a respective calibration offset for a respective force sensor.

In one or more embodiments, the method further comprises after the time period, obtaining respective subsequent data measurements from each force sensor; and determining respective resulting force measurements for each sensor by subtracting the respective calibration offset from the respective subsequent data measurements. In one or more embodiments, the method further comprises obtaining the respective data measurements from each force sensor over a predetermined ski-turn window that includes a predetermined number of ski turns.

In one or more embodiments, the method further comprises detecting when the user is skiing, wherein the respective statistic is based only on the respective data measurements that were obtained while the user was skiing. In one or more embodiments, the method further comprises performing steps (a)-(c) in response to a detection of a recalibration event. In one or more embodiments, the recalibration event comprises a temperature change that is greater than a maximum temperature change since a last calibration, an elapsed time that is greater than a maximum time duration since the last calibration, a detection of the user beginning to ski, a detection that the user has completed a ski turn, and/or a receipt of a manual recalibration request.

In one or more embodiments, the recalibration event comprises the detection that the user has completed the ski turn, the time period that the respective data measurements are obtained in step (a) includes the ski turn, and the method further comprises determining respective resulting force measurements within the ski turn for each sensor by subtracting the respective calibration offset from respective ski turn data measurements, the respective ski turn data measurements obtained during the ski turn. In one or more embodiments, the time period that the respective data measurements are obtained in step (a) includes the ski turn and a length of time before the ski turn, and the respective statistic determined in step (b) is of the respective data measurements that were obtained during the length of time before the ski turn.

In one or more embodiments, the method further comprises determining whether the user is performing a ski turn; and when the user is performing the ski turn, delaying the storing of the respective statistic as the respective calibration offset for the respective force sensor until the ski turn is completed. In one or more embodiments, the respective statistic comprises a minimum, a maximum, an average, a median, a percentile, and/or a statistical model of the respective data measurements.

Another aspect of the invention is directed to a method of calibration of a system designed for analysis of ground reaction forces of a user's feet, wherein the system comprises a left and right footwear each with a plurality of force sensors, the method comprising: (a) obtaining a respective data measurement from each force sensor; (b) comparing each data measurement to a respective calibration offset for a respective force sensor; (c) when the respective data measurement is higher than the respective calibration offset, returning to step (a) to obtain another respective data measurement from the respective force sensor; and (d) when the respective data measurement is lower than or equal to the respective calibration offset, storing the respective data measurement as a respective updated calibration offset for the respective force sensor.

In one or more embodiments, the method further comprises (e) storing a start time of a force-calibration time window; and (f) when the respective data measurement is lower than or equal to the respective calibration offset: storing the respective data measurement as the respective updated calibration offset; resetting the start time of the force-calibration time window; and returning to step (a) to obtain another respective data measurement from each force sensor.

In one or more embodiments, the method further comprises (g) determining an elapsed time of the force-calibration time window; (h) comparing the elapsed time to a maximum time window length; (i) when (1) the elapsed time is less than the maximum time window length and (2) the respective data measurement is lower than or equal to the respective calibration offset: storing the respective data measurement as the respective updated calibration offset; resetting the start time of the force-calibration time window; and returning to step (a) to obtain another respective data measurement from each force sensor; (j) when (1) the elapsed time is less than the maximum time window length and (2) the respective data measurement is higher than the respective calibration offset, returning to step (a) to obtain another respective data measurement from each force sensor; and (k) when the elapsed time is greater than or equal to the maximum time window length: determining a respective minimum data measurement from the respective data measurements obtained during the force-calibration time window; storing the respective minimum data measurement as the respective updated calibration offset; storing the time at which the minimum data measurement occurred as the respective start time of the force-calibration time window; and returning to step (a) to obtain another respective data measurement from each force sensor.

In one or more embodiments, the method further comprises performing steps (a) and (b) and step (c) or (d) in response to a detection of a recalibration event. In one or more embodiments, the recalibration event comprises a temperature change that is greater than a maximum temperature change since a last calibration, an elapsed time that is greater than a maximum time duration since the last calibration, a detection of the user beginning to ski, a detection that the user has completed a ski turn, and/or a receipt of a manual recalibration request.

Another aspect of the invention is directed to a system designed for analysis of ground reaction forces of a user's feet, comprising: a left and right insole each with a plurality of force sensors; one or more insole radio transceivers in electrical communication with the force sensors of each insole; and a mobile terminal comprising: a mobile radio transceiver in electrical communication with the one or more insole radio transceivers; a microprocessor electrically coupled to the mobile radio transceiver; and non-transitory memory electrically coupled to the microprocessor. The non-transitory memory stores computer-readable instructions that, when executed by the microprocessor, causes the microprocessor to (a) obtain respective data measurements from each force sensor over a time period while the user's feet are in the left and right footwear; (b) determine a respective statistic of the respective data measurements for each force sensor over the time period, wherein the respective statistic comprises a minimum, a maximum, an average, a median, or a percentile of the respective data measurements; and (c) store the respective statistic as a respective calibration offset for a respective force sensor.

In one or more embodiments, the computer-readable instructions, when executed by the microprocessor, further cause the microprocessor to detect that the user has completed a ski turn, wherein the time period that the respective data measurements are obtained in step (a) includes the ski turn; and determine respective resulting force measurements within the ski turn for each sensor by subtracting the respective calibration offset from respective ski turn data measurements, the respective ski turn data measurements obtained during the ski turn. In one or more embodiments, the time period that the respective data measurements are obtained in step (a) includes the ski turn and a length of time before the ski turn, and the respective statistic determined in step (b) is of the respective data measurements that were obtained during the length of time before the ski turn.

Another aspect of the invention is directed to a system designed for analysis of ground reaction forces of a user's feet, comprising: a left and right insole each with a plurality of force sensors; one or more insole radio transceivers in electrical communication with the force sensors of each insole; and a mobile terminal comprising: a mobile radio transceiver in electrical communication with the one or more insole radio transceivers; a microprocessor electrically coupled to the mobile radio transceiver; and non-transitory memory electrically coupled to the microprocessor. The non-transitory memory stores computer-readable instructions that, when executed by the microprocessor, causes the microprocessor to (a) obtain a respective data measurement from each force sensor; (b) compare each data measurement to a respective calibration offset for a respective force sensor; (c) when the respective data measurement is higher than the respective calibration offset, return to step (a) to obtain another respective data measurement from each force sensor; and (d) when the respective data measurement is lower than or equal to the respective calibration offset, store the respective data measurement as a respective updated calibration offset.

In one or more embodiments, the computer-readable instructions, when executed by the microprocessor, further cause the microprocessor to (e) store a start time of a force-calibration time window; and (f) when the respective data measurement is lower than or equal to the respective calibration offset: store the respective data measurement as the respective updated calibration offset; reset the start time of the force-calibration time window; and return to step (a) to obtain another respective data measurement from each force sensor.

In one or more embodiments, the computer-readable instructions, when executed by the microprocessor, further cause the microprocessor to (g) determine an elapsed time of the force-calibration time window; (h) compare the elapsed time to a maximum time window length; (i) when (1) the elapsed time is less than the maximum time window length and (2) the respective data measurement is lower than or equal to the respective calibration offset: store the respective data measurement as the respective updated calibration offset; reset the start time of the force-calibration time window; and return to step (a) to obtain another respective data measurement from each force sensor; (j) when (1) the elapsed time is less than the maximum time window length and (2) the respective data measurement is higher than the respective calibration offset, return to step (a) to obtain another respective data measurement from each force sensor; (k) when the elapsed time is greater than or equal to the maximum time window length: determine a respective minimum data measurement from the respective data measurements obtained during the force-calibration time window; store the respective minimum data measurement as the respective updated calibration offset; store the time at which the minimum data measurement occurred as the respective start time of the force-calibration time window; and return to step (a) to obtain another respective data measurement from each force sensor.

In one or more embodiments, the computer-readable instructions, when executed by the microprocessor, further cause the microprocessor to perform steps (a) and (b) and step (c) or (d) in response to a detection of a recalibration event. In one or more embodiments, the recalibration event comprises a temperature change that is greater than a maximum temperature change since a last calibration, an elapsed time that is greater than a maximum time duration since the last calibration, a detection of the user beginning to ski, a detection that the user has completed a ski turn, and/or a receipt of a manual recalibration request.

BRIEF DESCRIPTION OF THE DRAWINGS

A better understanding of the present invention can be obtained when the following detailed description of the preferred embodiment is considered in conjunction with the following drawings, in which.

Figure 1:
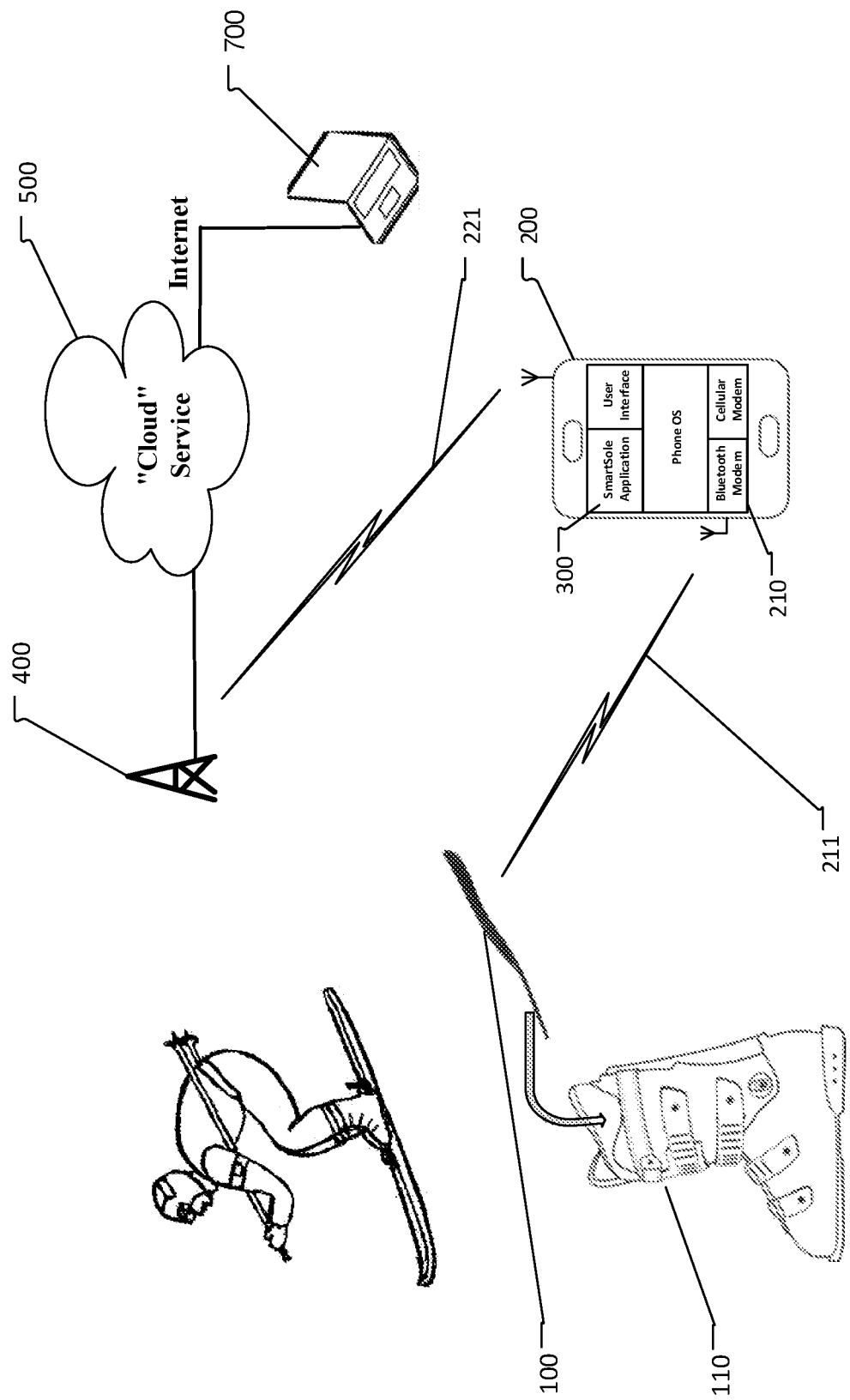
FIG. 1 is an exemplary ski boot haptic feedback system.

While the invention is susceptible to various modifications and alternative forms, specific embodiments thereof are shown by way of example in the drawings and are herein described in detail. It should be understood, however, that the drawings and detailed descriptions are not intended to limit the invention to the particular form disclosed, but on the contrary, the intention is to cover all modifications, equivalents and alternatives falling within the spirit and scope of the present invention as defined by the appended claims.

DETAILED DESCRIPTION

The following is a glossary of terms used in the present application:

Haptic Feedback System—in the context of this invention is a system able to collect and analyze motion of the ski boot and forces applied by the skier's foot to the sole of the ski boot, then after determination of the phase of the turn, apply a haptic feedback to the skier's foot indicating optimal distribution of the pressure points.

Application—the term "application" is intended to have the full breadth of its ordinary meaning. The term "application" includes 1) a software program, which may be stored in a memory and is executable by a processor or 2) a hardware configuration program useable for configuring a programmable hardware element.

Computer System—any of various types of computing or processing systems, including mobile terminal, personal computer system (PC), mainframe computer system, workstation, network appliance, Internet appliance, personal digital assistant (PDA), television system, grid computing system, or other device or combinations of devices. In general, the term "computer system" can be broadly defined to encompass any device (or combination of devices) having at least one processor that executes instructions from a memory medium.

Mobile Terminal—in the scope of this invention any wireless terminal such as cellular modem, cell-phone, smart-phone, etc. provisioned to operate in the cellular network.

Smart Phone—in the scope of this invention a computing device comprised of a wireless cellular communication port, a memory system, a processor configured to execute program instruction code contained in the memory system, a local and personal area wireless communication ports, a GPS receiver and user interface.

Memory Medium—Any of various types of memory devices or storage devices. The term "memory medium" is intended to include an installation medium, e.g., a CD-ROM, floppy disks, or tape device; a computer system memory or random access memory such as DRAM, DDR RAM, SRAM, EDO RAM, etc.; or a non-volatile memory such as a magnetic media, e.g., a hard drive, or optical storage. The memory medium may comprise other types of memory as well, or combinations thereof. In addition, the memory medium may be located in a first processor in which the programs are executed, or may be located in a second different processor which connects to the first processor over a network, such as wireless PAN or WMAN network or the Internet. In the latter instance, the second processor may provide program instructions to the first processor for execution. The term "memory medium" may include two or more memory mediums which may reside in different locations, e.g., in different processors that are connected over a network.

Cellular Network, in the scope of this invention a mobile communication network where the last link is wireless and the network is distributed over land areas called cells equipped with the fixed location base station radio transceiver providing the cell with the network coverage which can be used for transmission of voice, data, and other types of content.

Near Field Communication (NFC)—in the scope of this invention is a type of radio interface for near communication.

Personal Area Network (PAN)—in the scope of this invention, is a personal are network radio interface such as: Bluetooth, ZigBee, Body Area Network, etc.

Body Area Network (BAN)—in the scope of this invention is a network of sensors attached to the user body communicating over wireless interface.

Motion Monitoring System—in the scope of this invention is a system able to collect various instantaneous vectors such as: acceleration, angular orientation, geo-location and orientation, then using various mathematical operations to provide visual representation of the user's motion.

Ski Equipment—in the context of this invention, is any part of equipment used by the skier, such as: skis, ski boots, ski poles, ski clothing, ski glows, etc.

Equipment Parameters—in the context of this invention, is ski or snowboard design and manufacturing parameters, such as: length, weight, toe/center/tail, stiffness, etc. are extracted after manufacturing and entered into application.

Turn Symmetry—in the context of this invention the level of correlation between pressure levels and locations of the COF applied during the left and right turn.

User Parameters—in the context of this invention, is user's physical parameters, such as: weight, height, skiing competence level, etc. entered by the user into the application using mobile terminal user (UI) interface.

Software Program—the term "software program" is intended to have the full breadth of its ordinary meaning, and includes any type of program instructions, code, script and/or data, or combinations thereof, that may be stored in a memory medium and executed by a processor. Exemplary software programs include programs written in text-based programming languages, such as C, C++, Visual C, Java, assembly language, etc.; graphical programs (programs written in graphical programming languages); assembly language programs; programs that have been compiled to machine language; scripts; and other types of executable software. A software program may comprise two or more software programs that interoperate in some manner.

Topological Information—in the context of this invention, information about the topology of the ski slope obtained through any combination of techniques such as: topography maps, GPS, Radio-Telemetry, barometric pressure monitoring, etc.

User—in the context of this invention, person actively using haptic feedback system.

Point of Balance (POB)—in the context of this invention, a three primary points of contact between the foot and the ground located under 1st Metatarsal, 5th Metatarsal and the foot heel, also known as the foot triangle.

Center of Pressure (COP)—in the context of this invention is a point location of the vertical ground reaction force vector. It presents a weighted average of all pressures over the surface of the foot that is in contact with the ground.

Center of Mass (COM)—in the context of this invention is a point equivalent of the total body mass in the global reference system and weighted average of the COM of each body segment in 3Dimensional space.

Center of Force (COF)—in the context of this invention a point location of a force applied by skier's foot to the insole surface when the whole ski lies flat and in contact with the snow surface reaction force. Said force location is calculated from pressure data obtained from sensors located inside the ski boot insole and reflect neutral control of ankle muscle.

Ground Reaction Force—in the context of this invention, a force defined by Newton's third law of physics excreted by the ground on a body in contact with it. When person is standing the GRF corresponds with the person's weight and increases proportionally to acceleration when the person is moving. When the person is in motion, the GRF have two components—vertical and horizontal. This horizontal (or frictional) force is sometime referred as a shear force, and the ratio of magnitude of the horizontal force to the vertical GRF yields the coefficient of static friction/shear.

Natural Standing Position—in the context of this invention, it is a position when subject hip and knee joints are extended and in their most stable position and the line of gravity passes posterior to the hop and interior to the knee joints—position used to determine the subject's pronation.

Pronation—in the context of this invention, natural side-to-side movement of the foot during walk or run which starts in the first part of the gait stance phase.

Neutral Pronation—in the context of this invention, a position where the COM is acting inwards and being on the inside of the midline of the foot and the weight is distributed evenly over foot POB and all toes, with slight emphasis of big toe.

Under-pronation (Supination)—in the context of this invention, a position where the COM moves outwards and being outside of the midline of the foot and the weight is mostly distributed on the outside the foot and on the outer toes.

Over-pronation—in the context of this invention, a position where the ankle and the COM moves inwards and being inside of the midline of the foot and the weight is mostly distributed on the inside the foot and on the big toe.

Net Force—in the context of this invention, is the vector sum of forces acting on aa object or body. The net force is a single force that replaces the effect of the original forces on the particle's motion. It gives the particle the same acceleration as all those actual forces together as described by the Newton's second law of motion.

Moment; Moment of Force; Torque—in the context of this invention, a moment, moment of Force, or Torque is a measure of the tendency to cause a body to rotate about a specific point or axis. The magnitude of the moment of a force acting about a point or axis is directly proportional to the distance of the force from the point or axis, and is defined as: M=Force*Distance, or M=F*r.

1st Moment of Force—in the context of this invention, this is a location of a center of mass normalized by total mass.

2nd Moment of Force—in the context of this invention, or moment of inertia, and this is an angular mass of a ridged body which determines the force needed for acceleration.

Footwear—in the context of this invention, footwear comprises an item or items which protect or are worn by a user's foot or feet, such as athletic or dress shoes, boots, ski boots, slippers, etc. These footwear provide separation between the ground and the user's foot and includes the sole or soles of the footwear, including but not limited to, permanent soles, or removable insoles, allowing, among other activities, a user to be able to walk on gravel roads without presenting discomfort or injury to the user's foot or feet.

Motion Processor—in the context of this invention, a computing device configured to process algorithms designed to track object movements, from vectors obtained from a gyroscope, accelerometer and magnetometer.

Cloud Server—in the context of this invention is a computing equipment allowing a client application software to be operated using Internet enable devices.

Accelerometer—in the context of this invention is an inertia based device measuring acceleration component based on device motion and gravity.

Gyroscope—in the context of this invention is a sensor to measure an angular rate of change in device orientation irrespective to gravity.

Magnetometer—in the context of this invention is a sensor to measure magnetic field by computing the angle of the Earth magnetic field and comparing that measurement to the gravity measured by an accelerometer.

Pressure Sensor—Atmospheric—in the context of this invention is a sensor measuring the differential or absolute atmospheric pressure and used to track vertical motion.

Vector—in the context of this invention, a quantity which have a magnitude and direction and may be represented as an arrow. The examples of vectors are velocity vector, force vector, rotation vector, gravity vector, etc.

Force Sensor—in the context of this invention is a sensor (resistive, capacitive, etc.), used to measure pressure (in Netwons), which is converted to force using 2nd Newton Law.

Euclidian Space—in the context of this invention, any nonnegative integer dimension—including two and three-dimensional space, consisting of points, which are defined only by the properties that they must have for forming essentially one Euclidean space of each dimension, with all Euclidian spaces of a given dimension being isomorphic.

Euclidian Distance (2D)—in the context of this invention, a distance between two points in Euclidean space is the length of a line segment between the two points. It can be calculated from the Cartesian coordinates of the points using the Pythagorean theorem https://en.wikipedia.org/wiki/Pythagorean_theorem.

Euclidian Distance Matrix—in the context of this invention, a n×n matrix representing the spacing of a set of n points in k-dimensional space, where the elements distance are given by squares of their distances.

Rotation Vector—Angular Velocity—in the context of this invention is a vector quantity whose magnitude is proportional to the amount or speed of a rotation, and whose direction is perpendicular to the plane of that rotation.

Rotation Matrix—in the context of this invention is a matrix that is used to represent rotation in Euclidean space and to describe device orientation.

Gravity—in the context of this invention is Earth's gravity measured in m/s$^2$ and excluding acceleration caused by the user and consisting of a relative angle between device and gravity vector.

Orientation (attitude)—in the context of this invention is an orientation of the device expressed in Euler angles, rotation matrix or quaternion.

Motion Sensor Fusion—in the context of this invention is a method to derive a single estimate of device orientation and position by combining data from multiplicity of sensors.

Global Coordinate System—in the context of this invention is a x/y/z coordination system referenced to the earth magnetic field and in angle of inclination dependent on geographical location.

Local Coordinate System—in the context of this invention is a x/y/z coordinate of the motion sensor located ski boot, where the x-axis is a horizontal and points to the toe of the ski boot, the y-axis is a horizontal and points to the left and the z-axis is vertical and points up.

Orientation—in the context of this invention, the relationship between the directions of the local coordinate system and the corresponding directions of global coordinate system.

Euler Angles—in the context of this invention, are three angles introduced by Euler to describe orientation of a rigid object using sequence of three consecutive rotations user to represent orientation of the object in 3D space.

Quaternion—in the context of this invention is a mathematical expression used to calculate rotation state of the device using the axis and angle of rotation.

Azimuth—in the context of this invention, a horizontal angle measured from any fixed reference plane or easily established base direction line.

Ground Reaction Force (GRF)—in the context of this invention is the force exerted by the ground on a body equal to the person's weight time acceleration Zero Value—in the context of this invention it is a floating point number with the integer portion equal to "0" and the fractional portion equal to "0'.

Heading—in the context of this invention it is direction the x-axis of insole.

Coarse Gravity Value—in the context of this invention, an approximate value of natural gravity force equal 0.98066

Precise Gravity Value—in the context of this invention, a value of the natural gravity force at the GPS location coordinates the measurement is taken.

Sub-system—in the context of this invention, a unit of several devices comprising a functional part of the larger system. An example of said sub-system is a motion and force processing element comprising motion processor, three-axis accelerometer, three-axis gyroscope, three-axis magnetometer, multiplicity of force/pressure sensors and a haptic actuator.

Steering Angle—in the context of tis invention an angle between user body coronal plain and heading.

DESCRIPTION OF PREFERRED EMBODIMENT

The invention comprises a ski boot (or ice-skate boot) insole configured to measure distribution of forces transmitted to the ski boot insole during run, a 3D motion processing element, a linear resonant actuator to provide feedback to the skier's foot and a wireless personal are network (PAN) transceiver—such as: Bluetooth, ANT, etc., communicating force and motion data to the smart-phone based application. Based on the knowledge of skiing bio-mechanics, and the information received from the ski boot insole, the smart-phone based application predicts the intended ski trajectory, then provides haptic feedback to the foot of the skier, suggesting proper distribution of pressure points on the insole. Furthermore, the smart-phone application transmits the pressure and motion data obtained from the ski boot insole together with the GPS timing and coordinates to the remote location for post-processing using wireless cellular network. During post-processing, a 3D map based on GPS coordinates is retrieved and superimposed on the motion/pressure data, which may be provided in real-time on a remote computer or a smart-phone. Alternatively, post-processed data may be stored on the remote server and retrieved later by the user.

The insole of the present invention comprises several Microelectromechanical (MEMS) motion processor, providing capability of measuring motion in 10-degree of freedom. Said capabilities are enabled by integrating a 3-axis accelerometer, a 3-axis gyroscope, a 3-axis magnetometer (compass), and a barometric pressure sensor, then process the vectors obtained from said sensors by one of well-known motion fusion algorithms. In addition, to motion processing, two or more force pressure sensors are also embedded in the sole, said pressure sensors record the force applied to the pressure point on the insole. When the change in distribution—migration of the center of force (COF), is combined with the motion data, we can obtain the phase of the turn the skis are in, then scaling such results by user and equipment information (weight, height, ski side-cut radius, etc.), provide feedback to the skier's foot indicating timing of change and the amount of pressure necessary to obtain desired turn, while recording said pressure, motion and errors.

Most skiers have an intuitive understanding of skiing, gained from practice and understanding some of the physics behind skiing. Such understanding is useful to skiers of all levels, as it identifies key principles, enabling to properly execute certain movements to improve performance. In general, skiing (downhill), involves high speed run down the sloped terrain using quick turns. The skier gains speed by converting gravitational potential energy into kinetic energy of motion, so the more a skier descends down a heel, the faster he goes. A skier maximizes his speed by minimizing resistance to motion, both from air resistance and snow resistance. While the skier minimizes his air resistance (drag) by reducing his projected frontal area, the reduction of snow resistance requires combination of balance and subtle technique of turn. While the turn is essential to go around objects of gates and arrive safely at the bottom of the slope, the turn itself introduces resistance and as such slows the skier. This is particularly pronounced by less experienced skiers, as they skid around their turns and the skis are tilted on their edge and skis plow into the snow. Also, in some cases, a degree of skidding is unavoidable, more advanced skier, will attempt to carve around the turn using skis natural shape (side-cut), and flexibility. To help in "carving the turn", skier will tilt the skis on the inner edge of the turn, and in general, the larger is the angle between the snow and the ski surface, the tighter the turn is. When the ski is flat on the snow, the radius of the carved turn RT equals the side-cut radius RSC, and the ski turns without skid as it travels in the same direction as its velocity.

However, skid is an important technique used to suddenly change direction, slow the speed or even stop. And unlike carving where a skier eases into the turn, a skidded turn is initiated by simultaneously tilting the edge of skis into the snow and pivoting in the direction of the turn. This results in turning in that direction, due to the plowing effect, since the skis are pointed in a direction that is different from the initial velocity. The steering angle determines sharp is the turn, and the loss of velocity. A steering angle of zero results in the skier moving in a straight line with no turning and no slowing down. A steering angle of 90° results in the skier slowing down with no turning, since the force of the snow plowing into skis without sideway component necessary for turn.

By measuring motion of the foot with 9-degree or 10-degree of freedom, one can monitor motion in 3D, then using knowledge of skier and ski physical parameters predict the progress of motion by extrapolation.

In general, downhill skiing comprise straight skiing with a flat skis between two consecutive turns, and the intrinsic skill necessary for skiing is the maintenance of balance. Balance is maintained by the skier's foot, which through numerous joints, tendons, muscles provides receptive field for two main balance metrics—Center of Mass (COM) and Center of Pressure (COP). In this context, the process of skiing may be divided into three phases: 1st—initiate transition of balance (initiate turn); 2nd—ski flat (flat ski between turns); 3rd—rotate pelvic (start next turn). All these phases are initiated and maintained through changes in the distribution of foot COP and application of said pressure to the ski boot through the ski boot insole.

Without much generalization, it is possible to say that the COP during the turn is located on the outside foot of the turn, while during the flat ski phase (between turns), it is distributed evenly between both feet and the net COP lies somewhere between the two feet depending on the relative weight taken by each foot. Furthermore, we may say that the location of COP under each foot is a direct reflection of the neural control of the ankle muscles. The location of COP under each foot is a direct reflection of the neural control of the ankle muscles. Any movement that flexes the foot or toes downward toward the sole (plantar flexion), will move the COP toward back of the foot, while movement of the foot in upward direction (dorsiflexion), will move COP toward the front of the foot, the movement of foot inward (invertor), moves COP towards the outside of the foot.

The position of COP can be obtained by placing two or more pressure sensors in the ski boot sole, then synchronizing the changes in COP with the motion vectors obtained from the 3D motion monitor. The knowledge of place the COP is at the present time combined with the knowledge of past trajectory, present orientation in 3D space, motion vectors and the location of COP allows prediction of the future ski trajectory. Such trajectory may be changed or influenced by the change in pressure applied to the foot—thus influencing change of COP and in turn change of turn parameters. Such "advise" about the timing and need to change location of COP can be provided through feedback to the skier foot.

This invention describes a system capable of monitoring motion of the skier foot in relation to the snow, measuring the location and distribution of force—pressure point(s), inside the ski boot and provide haptic feedback to the skier's foot, instructing on the time and direction the center of force (COF) must be moved for the optimal execution of the current turn. Such system comprises a ski boot insole for processing of motion and to provide haptic feedback, a smart-phone based monitoring application communicating with the insole using Bluetooth (or other suitable), personal area network (PAN) wireless technology, and with the cloud based server using cellular wireless technology.

The exemplary system is presented in FIG. 1. Here an insole 100, of a ski boot 110, with an insole 100, communicates with a monitoring application 300, hosted in a smart-phone 200. The monitoring application 300 pre-processes the motion and pressure data, retrieves a GPS time and coordinates from the smart-phone and sends said data using smart-phone cellular radio interface 221, to the cloud service 500, for further post-processing, while the pre-processed motion and pressure data are used to provide haptic feedback to the actuator located in the insole. Based on GPS coordinates extracted from data, the cloud server retrieves 3D map of the area, then superimposes the graphical and numerical parameters of the run on said 3D map. This map, together with the graphical and numerical parameters of the run may be displayed on the remote computer or viewed on the user smart-phone.

Figure 2:
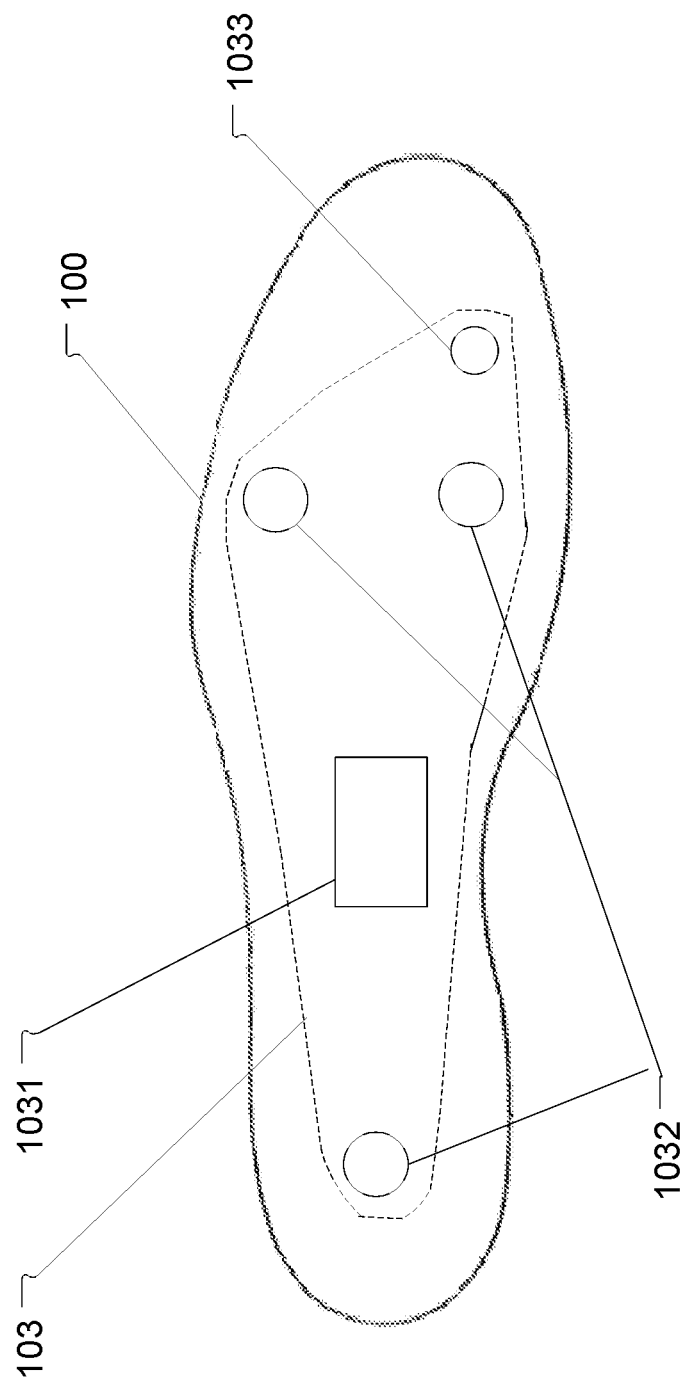
FIG. 2 depicts an innersole and the components of the exemplary haptic feedback system.
Figure 3:
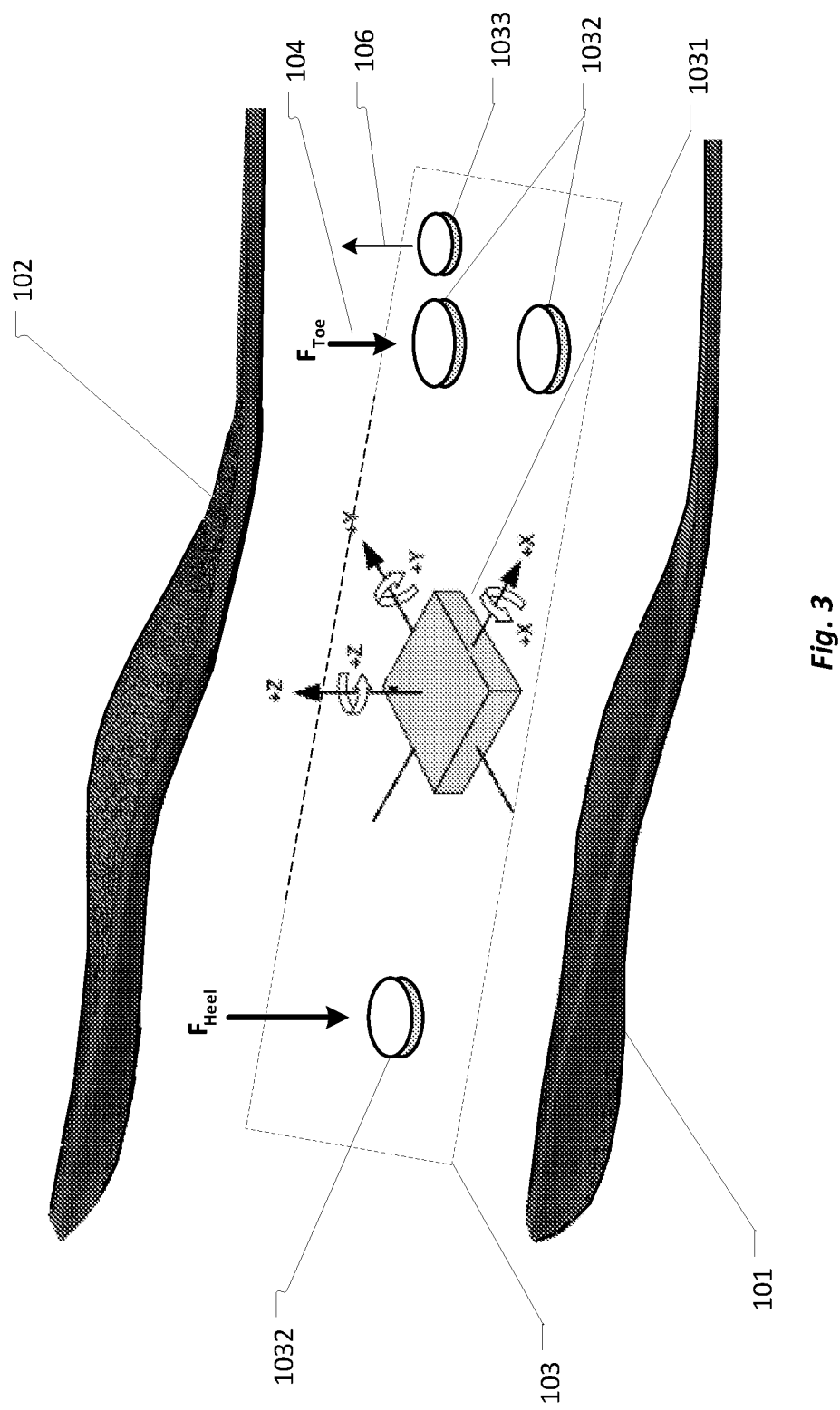
FIG. 3 presents a cross-section of the innersole.

Ski boot insole 100, presented on FIG. 2 and FIG. 3, comprises of a lower 101, and upper 102, insole surfaces and a motion processing and feedback sub-system 103, sandwiched in between insole surfaces. The motion and feedback sub-system consist of a motion processing element 1031, two or more pressure/force sensors 1032, and a haptic actuator 1033. The motion processing element 1031, is configured for analysis of motion with 10-degree of freedom comprising several inertial MEMS sensors: a 3D gyroscope; a 3D accelerometer; a 3D magnetometer (compass); and an atmospheric pressure sensor.

The 3D gyroscope is used to measure angular rate change by the insole in degrees per second, thus allowing measurement of angle, travel and as such, track changes in the insole orientation (pitch, roll and yaw angles). The accelerometer is used to measure acceleration of the insole caused by motion due to gravity in an X, Y, Z coordinate system by computing the measured angle of the device, compared to gravitational force and the results are expressed in m/s2. By integrating acceleration vector, a(t) over period of time, we obtain velocity function v(t). The 3D magnetometer measures the earth magnetic field at specific location. By computing the angle of the magnetic field, and comparing that angle to gravity obtained from accelerometer, we are able to determine the orientation of the insole with respect to magnetic North. Beside, sensing the direction of earth magnetic field, magnetometer is used to eliminate drift of gyroscope. Furthermore, the insole motion processing element employs an atmospheric pressure sensor to obtain changes in the altitude and rate of descent by detecting ambient air pressure ($P_{amb}$) according to equation:

$$h_{alt} = \left(1 - \left(\frac{P_{amb}}{10132}\right)^{0.190284}\right) \times 145366.45$$

to track vertical motion.

By observing three-dimensional vector of gravity measured by the accelerometer along with measurements provided by gyroscope, we can determine orientation of the ski (pitch, roll, yaw), while the skier is in motion. Also, by subtracting gravity vector form acceleration, we obtain linear acceleration of the ski. The orientation angles describe motion and are used to provide graphical representation of motion. Furthermore, we derive a rotation vector from results provided by accelerometer, gyroscope and magnetometer. This vector represents a rotation around a specific axis and corresponds to the components of a unit quaternion, which represents yaw, pitch and roll and is used to graphically represent motion of the insole.

The quaternion of the insole (and ski boot), is calculated by, first converting gyroscope angular rate to a quaternion representation:

$$\frac{dq(t)}{dt} = \frac{1}{2}\omega(t)q(t)$$

where ω(t) is the angular rate of motion and q(t) represents normalized quaternion. Then, we convert the accelerometer results from local coordinate system, represented as AL to global coordinate system, represented as AG, by using previously obtained quaternion as:

$$A_G(t)=q(t)A_L(t)+q(t)'.$$

Then calculate acceleration quaternion as:

$$qf(t)=[0A_{G_y}(t)-A_{G_z}(t)0]\times gain$$

which is added as a feedback term to quaternion from gyroscope, then add magnetometer data to the azimuth (yaw) component of the quaternion.

Figure 4:
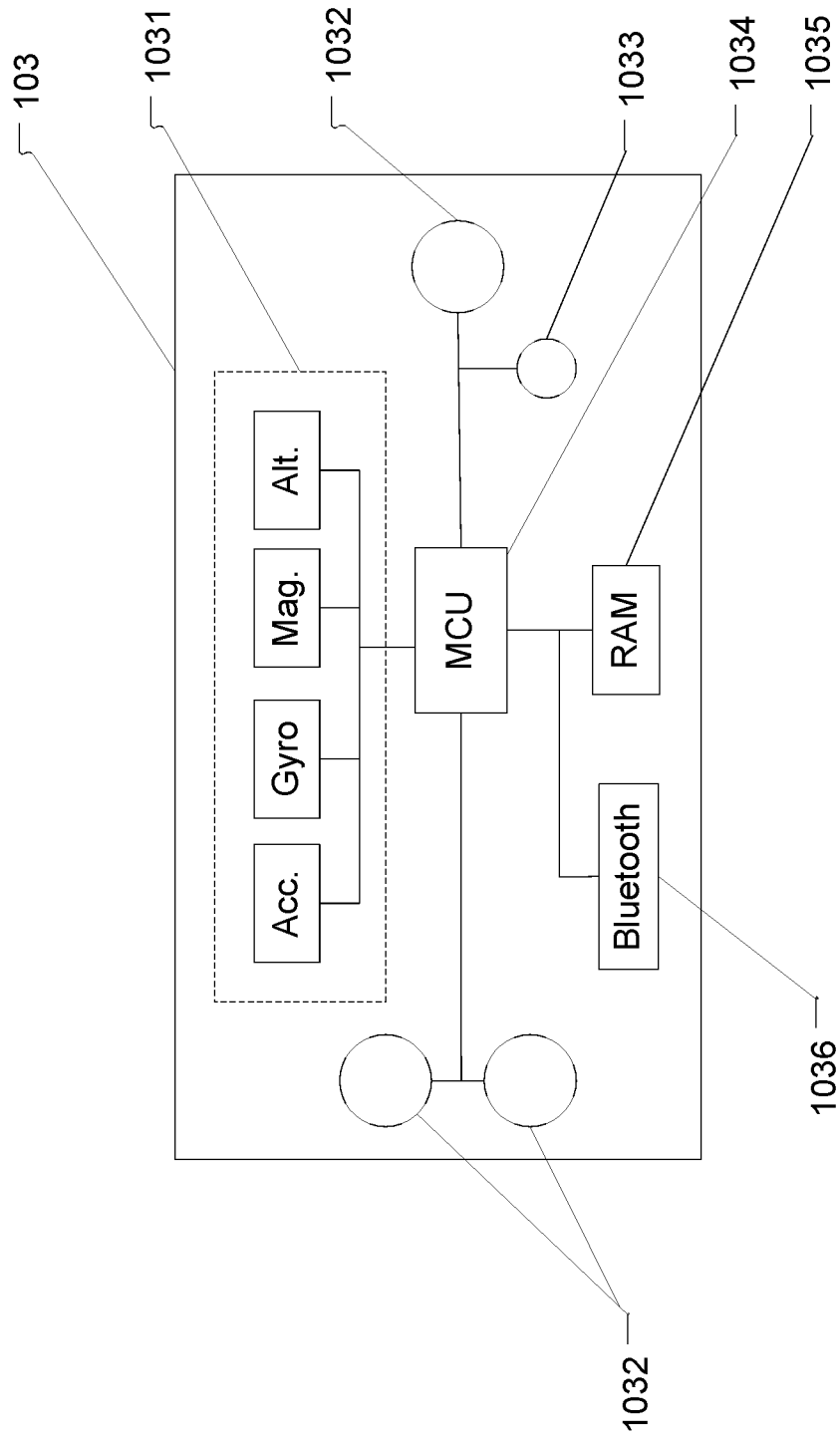
FIG. 4 presents relation between the skier's foot and the components of the ski boot innersole.

The exemplary ski boot insole motion processing and feedback sub-system 103, is presented in FIG. 4, and comprises of: a motion processing element 1031, comprising a 3-axis accelerometer, a 3-axis gyroscope, a 3-axis magnetometer and a barometric pressure sensor. In addition, the motion processing and feedback sub-system consist of several force pressure sensors 1032, a haptic feedback actuator 1033, a Bluetooth RF interface 1036, and microprocessor 1034 with its program memory 1035. The sensors within the motion processing element 1031, are connected to the microprocessor 1034 using one of appropriate digital interfaces, such as I2C, or an appropriate analog interface. Similarly, the force pressure sensors may be connected to the microprocessor analog-to-digital (ADC) converter using appropriate analog interface or directly to the microprocessor digital interface, while the haptic feedback actuator may be connected to the microprocessor digital-to-analog (DAC) converter.

Figure 5:
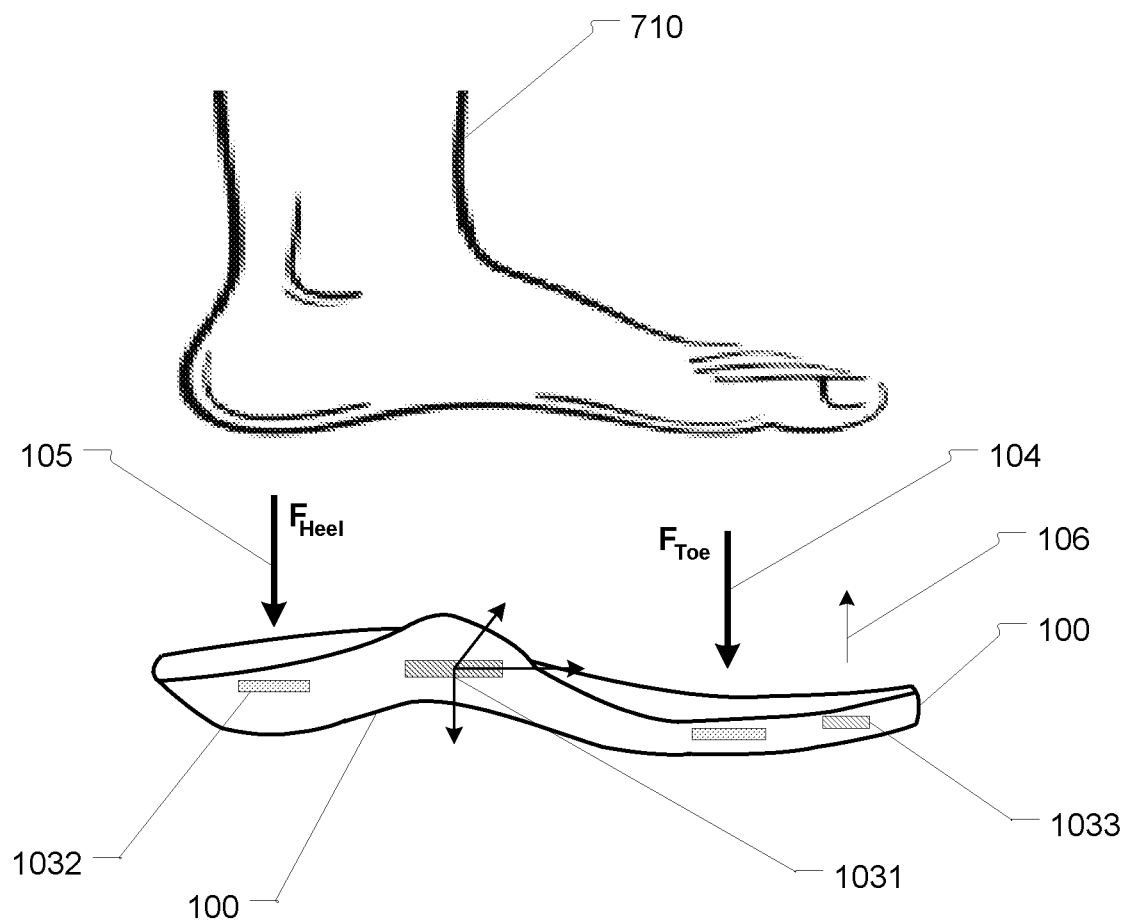
FIG. 5 depicts an exemplary architecture of the haptic system controller.

The relation between skier's foot 710, and the ski boot insole 100, is presented in FIG. 5. During the run, the location of the pressure points to the ski boot/ski and the distribution of pressure (force) between both feet provides the kinetic mechanism necessary to initiate and end a turn. While between turn—frequently referred a 'flat ski', the force is distributed equally between both feet and equally between front and back of the foot, the location of the pressure points between the feet and inside the ski boot changes during the turn. From FIG. 5, one may observe two main location of the force—at the front of the foot ($F_{Toe}$) 104, and the back of the foot ($F_{Heel}$) 105. The actual location of those pressure points and consequently the location of center-of-force (COF) may be measured by two or more force sensors 1032. The haptic feedback 106, to the skier foot is provided by actuator 1033.

Each turn in skiing may be separated into three phases: 1) ski flat phase; 2) start of transition phase; 3) pelvic leg rotation phase. During the ski flat phase, the skier COF is distributed evenly between both skis and located in a neutral point (evenly distributed between toe and heel of the insole). The skier selects inner ski—effectively selecting direction of the turn—and starts the transition phase. At this moment, the COF of the inner foot migrates toward the pinky toe and initiated forward movement on the "new" outer ski, this moves the COF of the outer foot toward the big toe. Then enters the third phase by rotating his leg pelvic moving the COF firmly on the outer ski which places the resulting force FR on the edge of the outer ski.

Figure 6A:
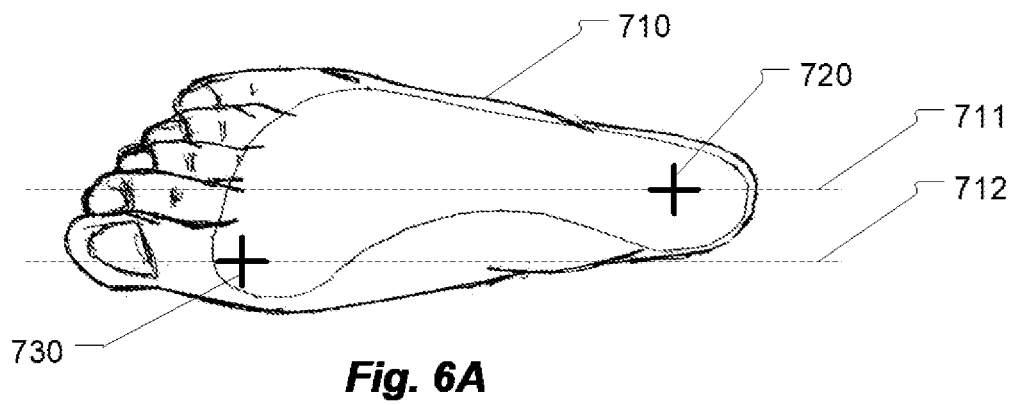
FIG. 6A presents skier foot bio-mechanical pressure points.

For the outer ski, this process is presented in FIGS. 6A, 6B and 6C and described below. In FIG. 6A, the foot 710, during the flat ski phase between edge change, the pressure is distributed evenly between two main mechanical points 720 located at the heel on the centered axis 711, and on the center of head of the 1st metatarsal (MT) bone 730, of a foot and centered along the inside edge 712.

Figure 6B:
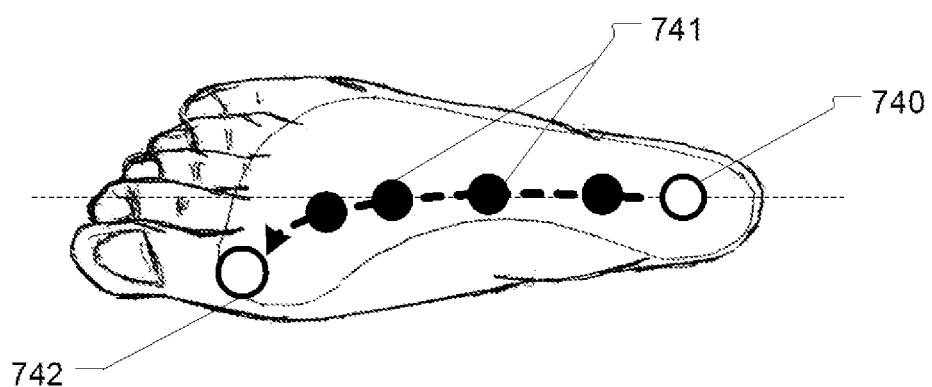
FIG. 6B presents the center of force (COF) point under the heel and its forward transition to become center of pressure (COP) in the phase between two consecutive turns.
Figure 6C:
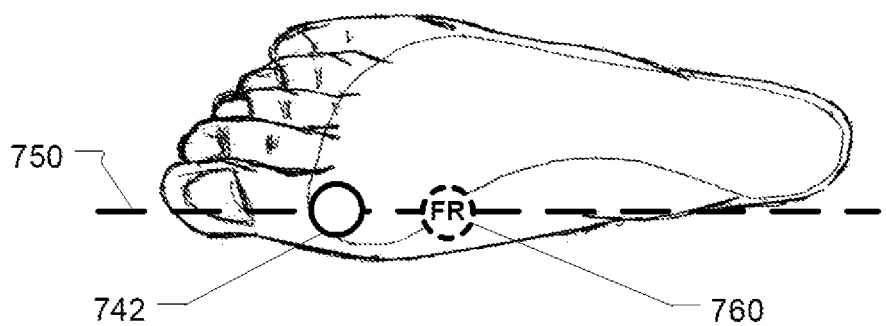
FIG. 6C presents the COP position at the end of the turn when it lays over the top of the inside ski edge and on the same axis as the center of mass (COM) resulting force (FR)

The start of transition is presented in FIG. 6B, here, when the COF 740 is located under the skier heel and progresses forward to position 742, —the head of the 1st MT. The COF essentially "rolls" inwards, the ankle is plantar flexed and the foot is inverted, the leg rotates while COF moves forward along arc 741, towards the head of the first MT. When the head of the first MT is maximally loaded (FIG. 6C), the COF and the skier fully rest on the outer foot (monopodial stance), while the resulting force FR 760 align with the COF above the edge of the outer ski 750. At this moment, the rolling of the foot inwards generates torque, which is directed into turn.

Figure 7A:
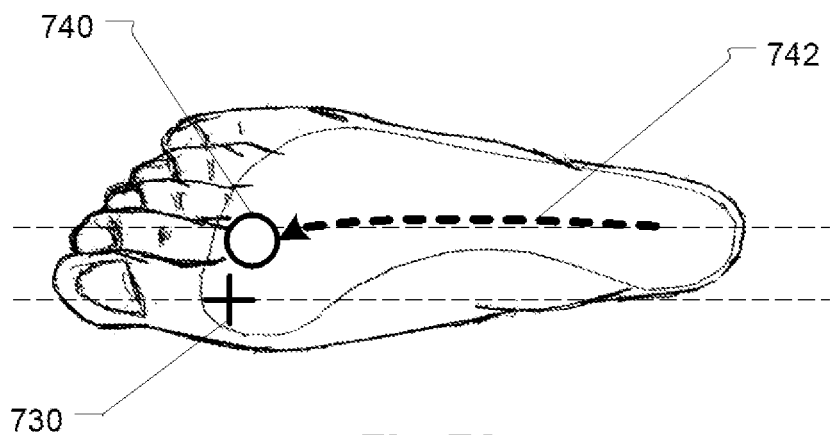
FIG. 7A presents the incorrect migration of the COF during turn from the foot heel to the head of the second toe.
Figure 7B:
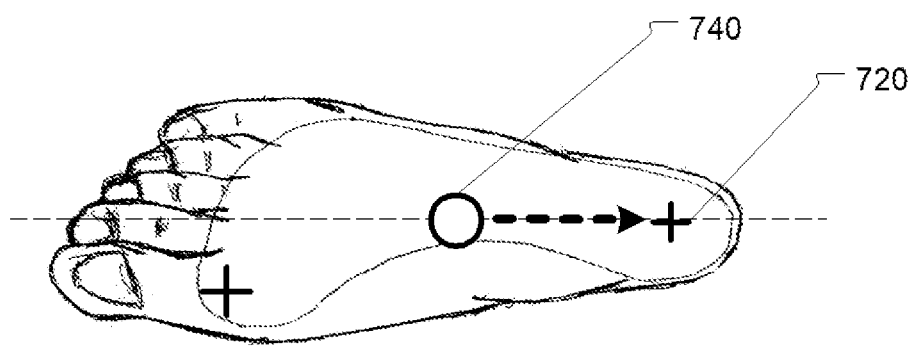
FIG. 7B presents the migration of the COF back from the incorrectly placed COF to the center of the foot and back to the heel.

When the distribution of pressure between skis or the transition of COF from the heel of the outer foot to the head of 1st MT fails, the turn is unsuccessful and skier loses his balance. The graphical representation of such turn is presented in FIGS. 7A and 7B. At some point between the edge change but before the new outside ski attains significant edge angle (without necessary plantar flex of an ankle), a moment develops between the inside edge of the ski and the COF resulting in inversion moment of force. Torque associated with vertical axial rotation of the leg, FIG. 7B, will reverse the movement of the COF 740, to the point of origin 720 as it is aligned with the heel and lower limb. Such reverse can't be stopped and skier loses his balance.

Figure 8:
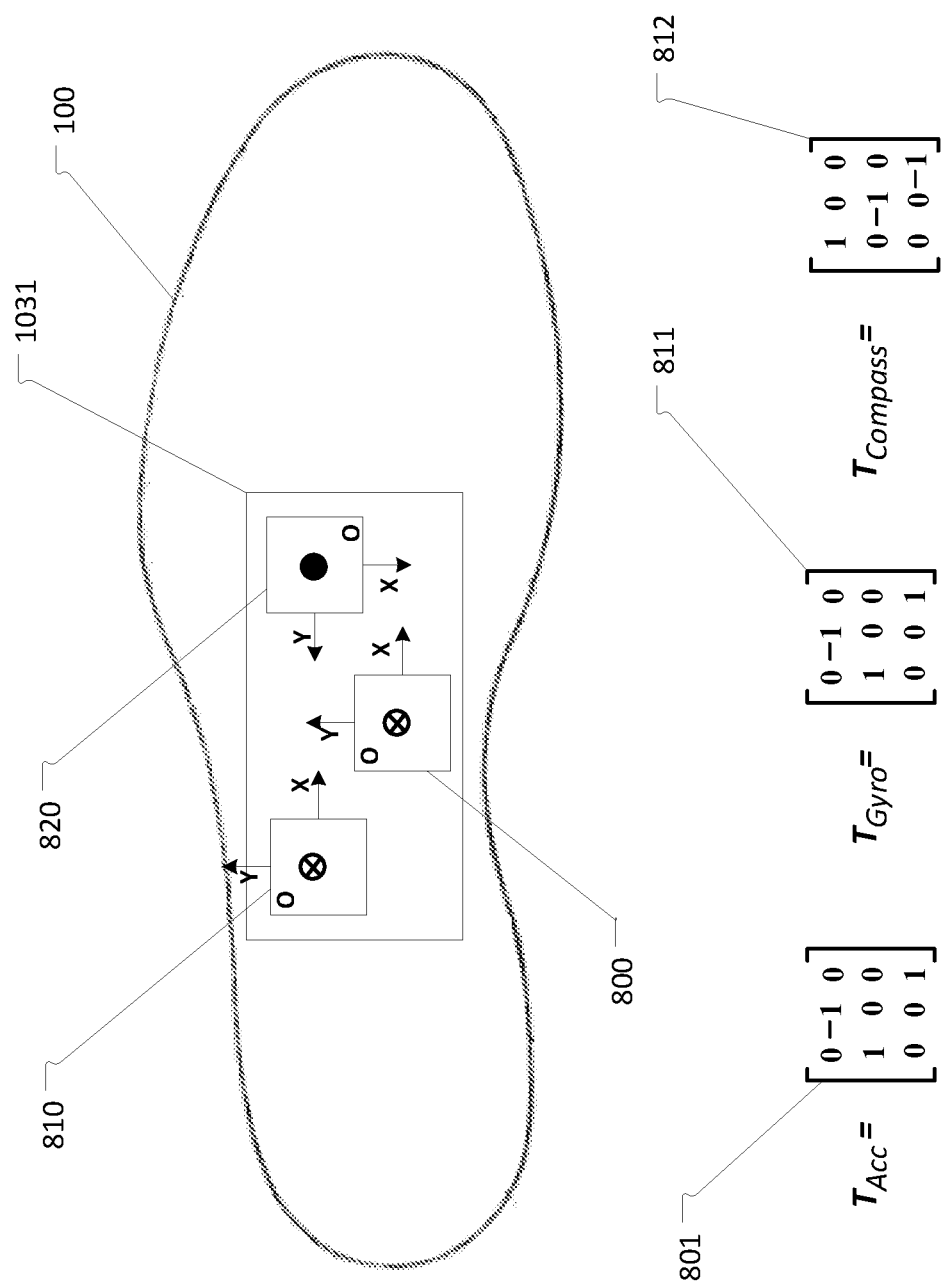
FIG. 8 presents the orientation of the motion sensors (accelerometer, gyroscope, magnetometer), and their transformation matrixes.

An exemplary orientation of motion sensors within the insole and its relation to their respective matrix is presented in FIG. 8. This relation is important to establish local coordinate system, as the matrix obtained from different sensors will rotate depending on insole orientation in reference to the global coordinate system. The motion processing element 1031, embedded in the ski boot insole 100, and comprises of: 1) an accelerometer 800, which Y axis points to the left side of the insole, the X axis points to the front of the insole and the Z axis points up; 2) a gyroscope 810, which Y axis points to the left side of the insole, the X axis points to the front of the insole and the Z axis points up; and a magnetometer 820, which Y axis points to the back of the insole, the X axis points to the right of the insole and the Z axis points down. Related to this orientation of sensors are respective matrixes: 801, 811 and 812.

The insole global coordinate system is established in reference to the earth magnetic field at the specific geographical location obtained from the magnetometer 820, by comparing its angle to gravity measured by accelerometer.

Figure 9:
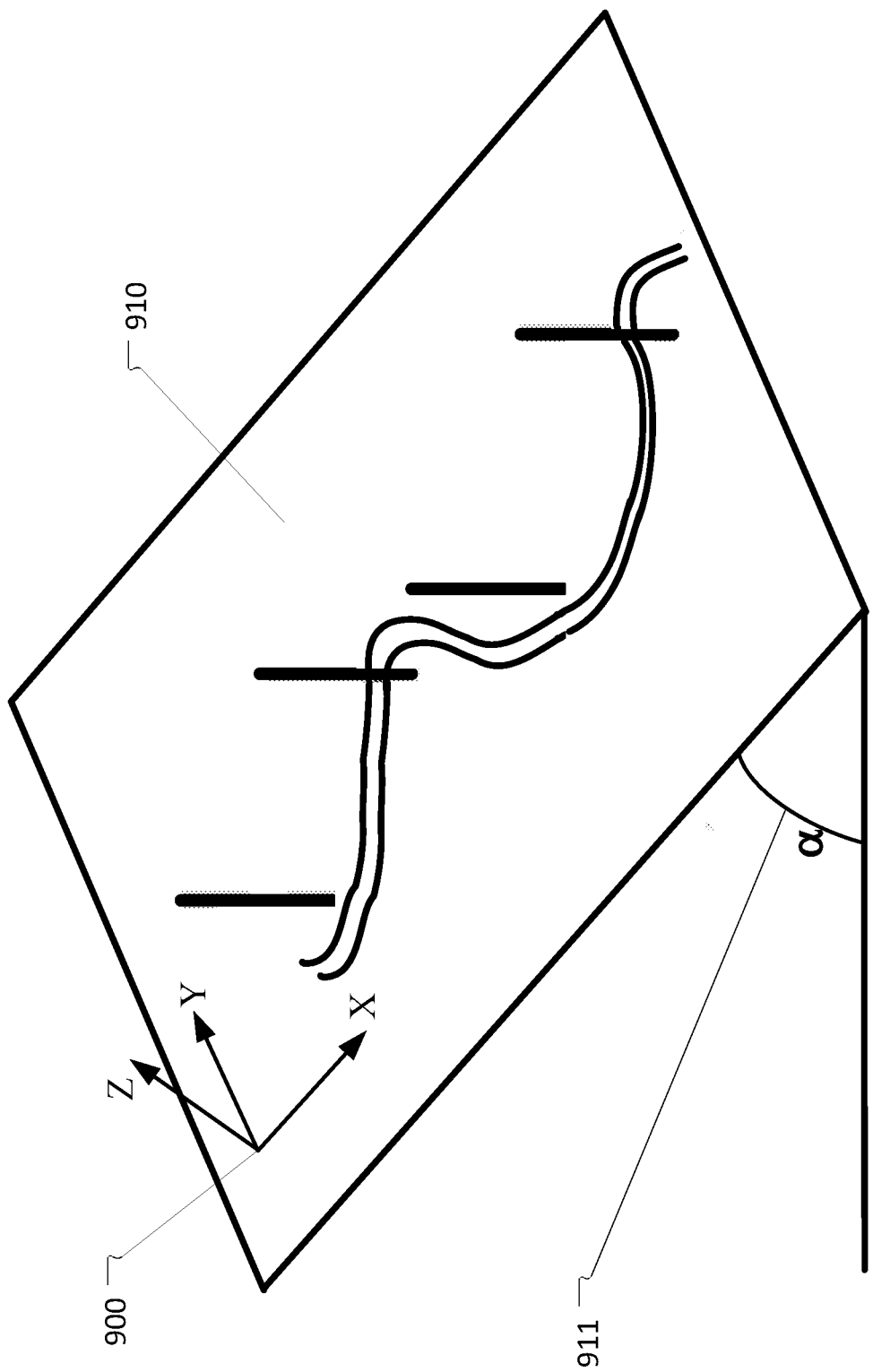
FIG. 9 presents the view of global coordinate system in relation to ski slope.
Figure 10:
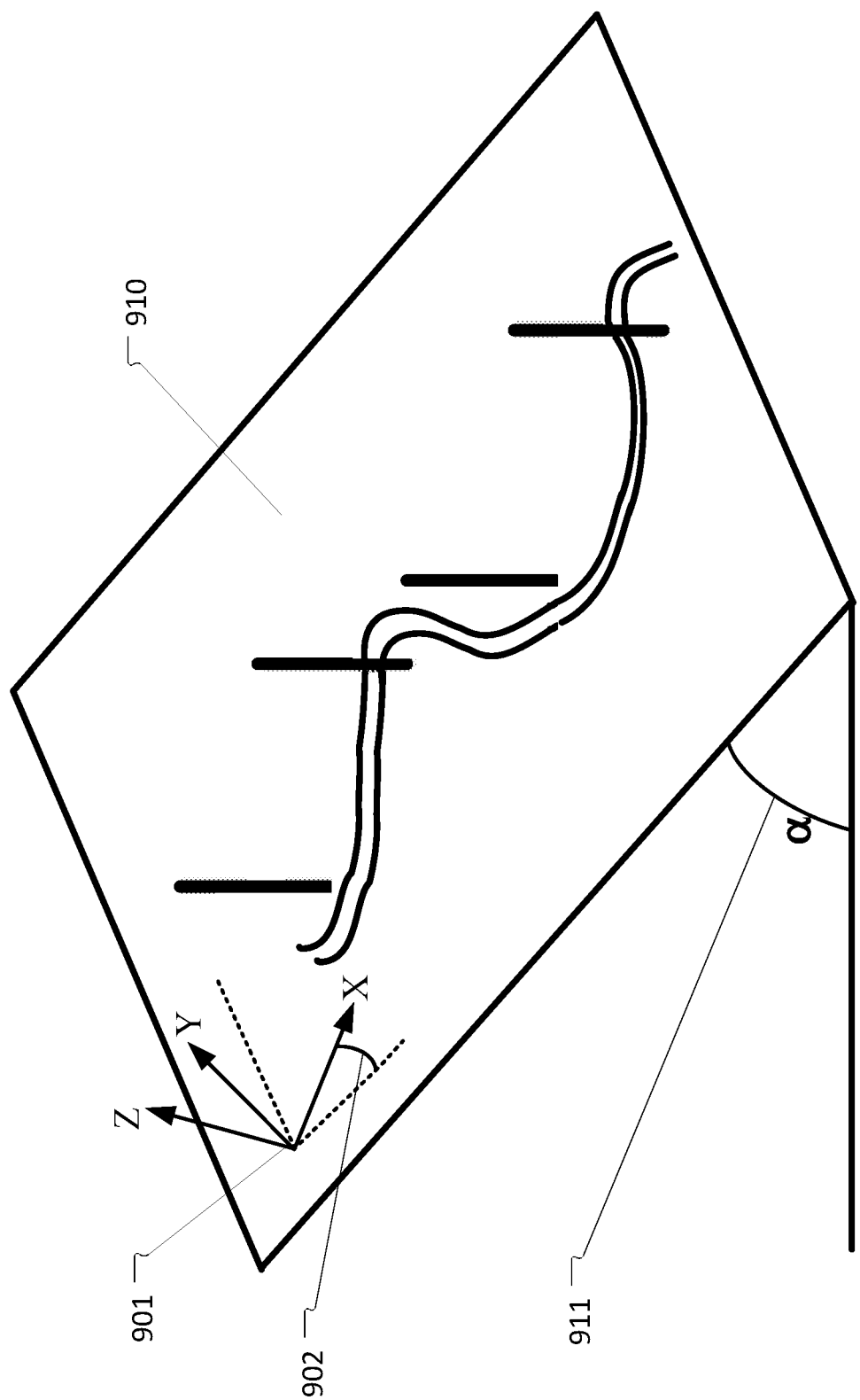
FIG. 10 presents the view of local (ski boot) coordinate system in relation to the ski slope.

The orientation of the global coordinate system 900, to the slope 910, with an incline a 911, is presented in the FIG. 9. Here, the Z axis is perpendicular to the ground and the negative Z points in direction of earth gravity. The X axis points to East and the Y axis points to magnetic North. After the global coordinate system is established, the local coordinate system 901 in FIG. 10, a coordinate system of the insole in relation to the global coordinate system may be calculated by reading measurement form accelerometer and gyroscope.

Figure 11:
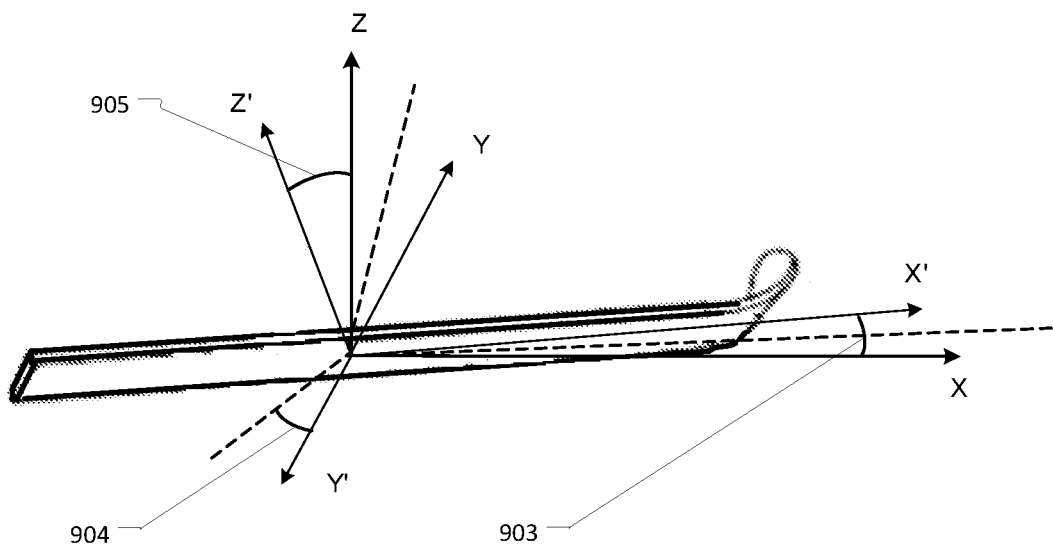
FIG. 11 presents transformation of local coordinate system during turn.

The method of presenting motion and orientation of the insole and by extension ski in the 3D space can be explained based on FIG. 11 and the processing allowing visualization of said motion described in the following sections. Here at time t0, the ski is flat and with the X axis pointing horizontally in the direction of slope line. The Y axis points to the left, while the Z axis point upward. After start of transition, at time $t_1$, ski rotates along the Z axis by angle $\Psi$ (yaw), 905, and along the X axis by angle $\theta$ (pitch), 903, and along the Y axis by angle $\phi$ (roll), 904, into left turn. This motion may be described in terms of Euler Angles using Euler motion theorem as three consecutive rotations of coordinate system xyz$\Rightarrow$'''y'''z'''$\Rightarrow$x''y''z''$\Rightarrow$x'y'z', where the 1st rotation is along the z-axis, the 2nd rotation is along the former x-axis, and the 3rd rotation is along the former y-axis.

The insole orientation may also be described in terms of matrix rotation. For a 3D matrix the rotation $\theta$ (pitch), may be described as:

$$R_\theta = \begin{bmatrix} \cos\theta & -\sin\theta & 0 \\ \sin\theta & \cos\theta & 0 \\ 0 & 0 & 1 \end{bmatrix}$$

so the vector $V_0=[1,2,0]^r$ will become $v'-[\cos\theta, \sin\theta, 0]^r$. As the rotation matrix are orthogonal with detriment 1 and with own transpose and an inverse, the rotation matrix will reverse its rotation when multiplied with the rotation inverse. We can also use the matrix rotation to obtain direction of earth gravity in relation to orientation of the insole. When the insole change orientation, its Z axis moves from z to z' by rotation matrix A, according to: z'=A*z. As for the local (insole) coordinate system the z' vector is $[0,0,0]^r$, the vector z is obtained by the inverse of rotation matrix.

Rather than use computationally intensive matrix rotation to obtain insole orientation, we may use mathematical expression of quaternion to calculate insole rotation state according to Euler's rotation theorem stating that device orientation may be expressed as rotation about one or more axis. This axis representing unit vector magnitude and angle remains unchanged—except for the sign, which is determined by the sign of the rotation axis represented as three-dimensional unit vector $\hat{e}=[e_x, e_y, e_z]^r$, and the angle by a scalar a.

Calculation of quaternion requires only four terms when the axis and angle of rotation is provided. Quaternion extends complex numbers from two-dimensions to four-dimensions by introducing two more roots of −1 as:

$$i^2=j^2=k^2=ijk=-1$$

which are then multiplied with real components as:

$$r+ix+jy+kz$$

then conjugate and normalize to arrive with unity |u|=1, or quaternion.

Calibrating Motion and Force Analysis System

Figure 12:
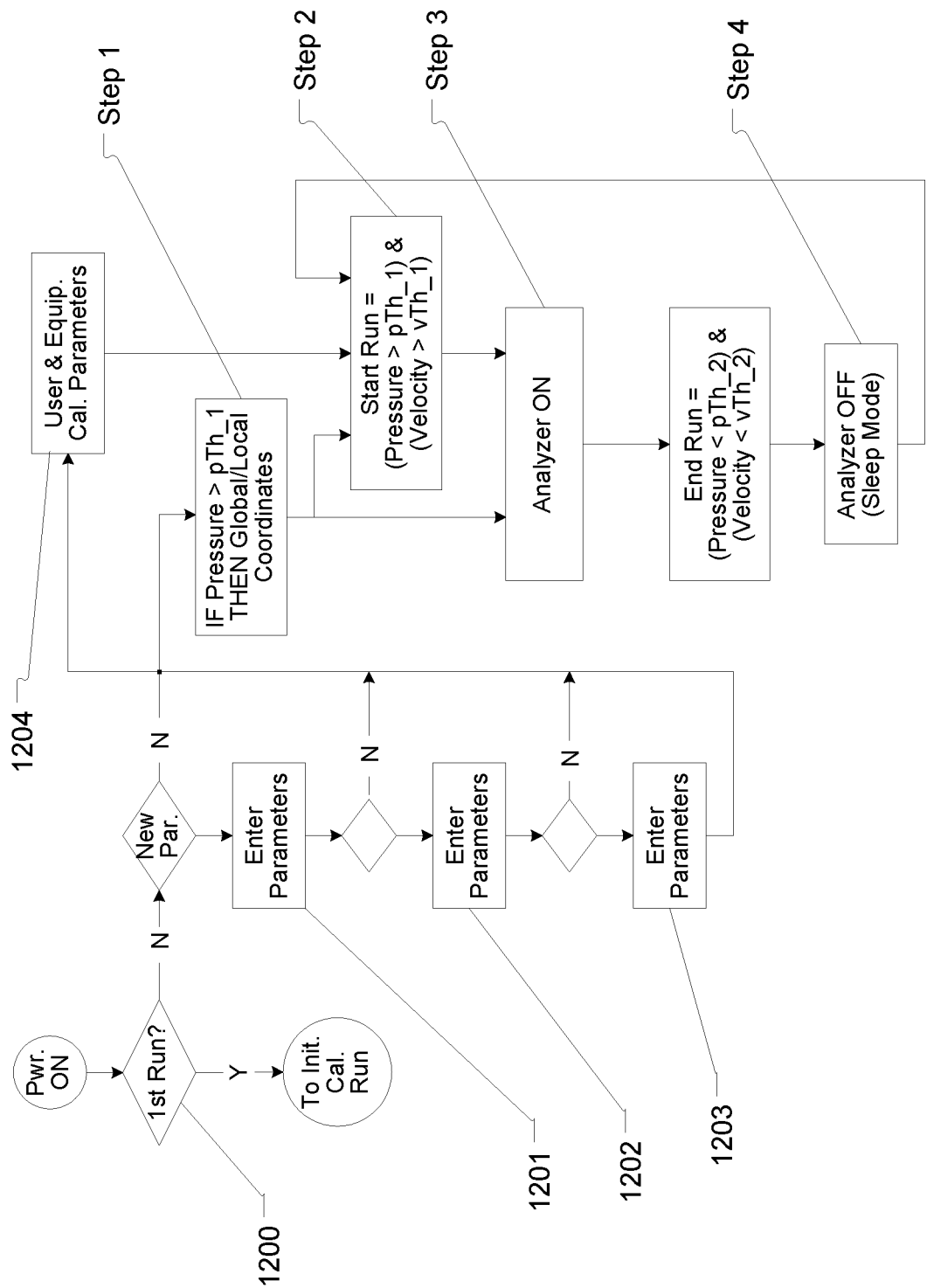
FIG. 12 presents a control process of the haptic feedback system.
Figure 13:
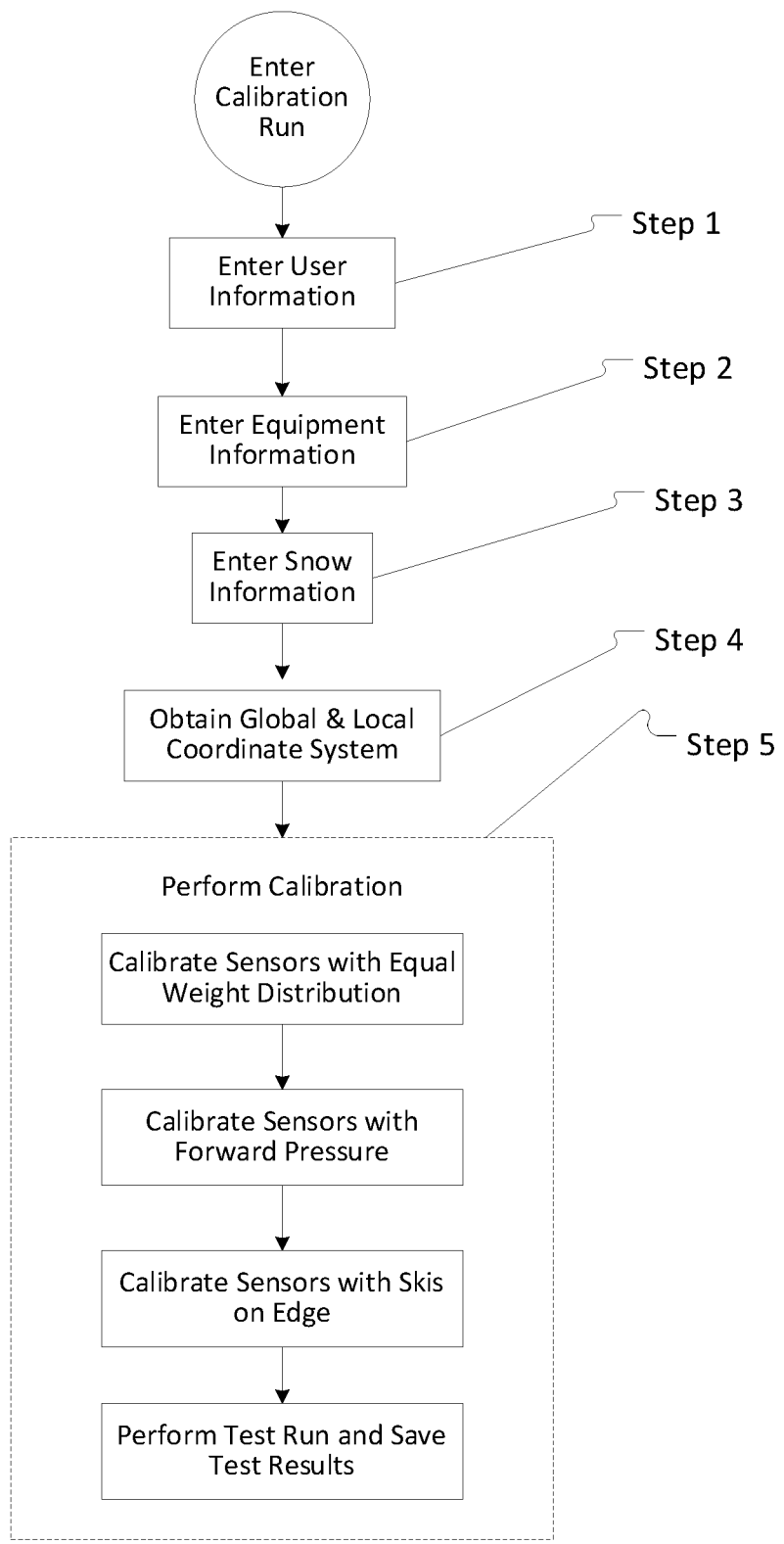
FIG. 13 presents the flow of the haptic system initial calibration.

Operations and procedures of said system are presented in FIGS. 12 and 13 and described in detail in the following sections. In FIG. 12, upon initial power-up and association of the insole Bluetooth transceivers with the application, the system control program checks if this is a 1st run 1200, indicating the initial calibration procedure was executed. Depending on user parameters, such calibration may be performed during the first run of the day, or at the request by the user, to allow for adjustments to the changing snow conditions, etc. If this is the 1st run of the day, the application enters the initial calibration routine of FIG. 13, otherwise, the user is given an option to update via the smart-phone user interface (UI), to update one or all system parameters. If said option is rejected, the application enters the main control loop, otherwise, the user is prompted to select which information—first (user parameters), second (equipment parameters), or third (snow condition parameters).

The First information 1201 comprises user parameters consisting among the others: body weight; height; and skiing proficiency level—"beginner", "intermediate", "advanced", "professional".

The Second information 1202 comprises technical parameters of the user equipment, consisting among the others: length of the ski; ski natural turn radius (side-cut); etc.

The Third information 1203 comprises the snow conditions present during the calibration run, such as, for example: "groomed slope", "icy", "powder". This information is used to derive two coefficients. First, to scale the time between the start of transition and when the COF reaches position 742 (see, FIG. 6B); second, to scale the distribution of COF between the inner and outer ski.

The second and third information may be manually entered by the user or scanned into the application from the QR-code or NFC parameter tag attached to the ski equipment.

The initial calibration procedures comprises steps which are described in FIG. 13, and in the following paragraphs.

In Step 1, the user is instructed to enter his or her physical parameters, such as weight, which is used to calculate the distribution of force between both skis using Newton's Second Law as well as calculating distribution of force inside the ski boot.

In Step 2, the user enters equipment parameters by either scanning a QR-code or an NFC tag attached to the equipment or by manually using the smart-phone UI. Among others, some of parameters, like the length and the turning radius or, side-cat of the ski are important factors that are used in conjunction with motion vectors to calculate the ski effective turning and to derive an optimal turning radius during turns.

In Step 3, the user enters the current snow condition of the slope. This is used to appropriately scale the pressure point (weight) distribution and timing of COF changes in different conditions of the slope, for example a change of technique between powder skiing and skiing on icy snow.

In Step 4, the application instructs the user to step into the skis and reads data from motion sensors for the purpose of establishing a global and a local coordinate system.

Step 5 instructs the user to perform several exercises:
1) Stand in a normal, relaxed bi-pedal position with body weight equally distributed between both skis, then record the force [N], measured by each pressure force sensor;
2) Stand in a crouching position, leaning forward and elbows resting on the knees, then record the force [N], measured by each pressure force sensor;
3) With both skis parallel and without support of the ski pole, bend knees and push inward (as, for example, during sharp turns with both skis on the edge), then record the force [N], measured by each pressure force sensor;
4) Instruct the user to make a run consisting at least four carved turns. Allow for the ski to accelerate by ignoring first two turn, then record motion parameters during two consecutive turns; and
5) End the calibration procedure.

In practical terms it may be assumed that a system embedded in a footwear, or in footwear insoles which are designed to analyze motion and GRF comprising a motion processing element with 9-degrees of freedom and plurality of force sensors is calibrated when the algorithms employed in such analysis possess information of the relative orientation of the motion processing element (that is, the difference between the actual orientation of the motion processing element embedded in said footwear and the global coordinate system—Earth magnetic field). In simple terms, when properly calibrated, the difference between Earth magnetic vectors (as measured by the three-axis magnetometer) and gravity vectors (as measured by the three-axis accelerometer) will be "0.00", and the three-axis accelerometer shall record values: 0.00; 0.00 for the x-axis and the y axis. The value of natural gravity at the current location will be approximately equal to 0.9806 for the z-axis. Similarly, the difference between the Earth magnetic field vectors obtained from the three-axis magnetometer and the angles of orientation vectors obtained from the three-axis gyroscope shall be "0.00".

Similarly, each force sensor embedded in the footwear records exactly the force value which is currently applied to each force sensor. Alternatively, the same calibration effect can be achieved by recording the difference between measurements obtained from the force sensors while the measurements are obtained in a controlled environment, and then subtracting the differences from data samples received from each respective force sensor.

However, due to errors introduced by the fabrication of motion processing sensors and force sensors sub-system and the insoles, numerous inaccuracies may be introduced. Some of the sources of these inaccuracies are as follows: misalignment in assembly of motion sensors on a printed circuit board (PCB); misalignment in assembly of PCB containing motion processing sensors in the insoles; misalignment of force sensors in the insoles, the force sensors tolerances and different thicknesses of insole material between the user's foot and the force sensors; misalignment of the insoles in the footwear, physical characteristics of the footwear—for example, ski-boots or running shoes may have heel sections that are thicker than the sections at the toe, or an orthopedic shoe may have certain deformation of the sole to accommodate for physical characteristics of the user's stance, such as: over-pronation or under-pronation, or injury related changes to a user's physical stance. Calibration of each sensor during each step of the insole assembly process is time consuming, impractical and prone to a cumulative nature of errors. In essence, while the magnetometer will naturally align with the Earth's magnetic field, a slight tilt of the accelerometer along its x-axis will result in a y-axis vector to be larger than 0.00—if tilted left, and smaller than 0.00—if tilted right, while at the same time there will be difference between the angle of the accelerometer z-axis and the magnetometer z-axis and the value reported on the z-axis of the accelerometer will not be equal to the Earth magnetic field present at the current location.

The procedures of step 4—obtaining the Global Coordinate System—orientation of the footwear in relation to the Earth magnetic field, and the determination of the Local Coordinate System—orientation of the motion processing element in relation to the Global Coordinate System, was described in detail in the previous sections in relation to the processing of motion data. For clarity, we repeat part of this description as it relates to the calibration procedures.

The process of obtaining the Global Coordinate System was described above with reference to FIG. 9. The Global Coordinate System is obtained by computing the angles of the magnetic field vectors obtained from the three-axis magnetometer and comparing them to angles to gravity obtained from the three-axis accelerometer, which measure acceleration due to gravity in an x, y, z coordinate system by computing the measured angle of the device as compared to gravitational force.

Figure 18:
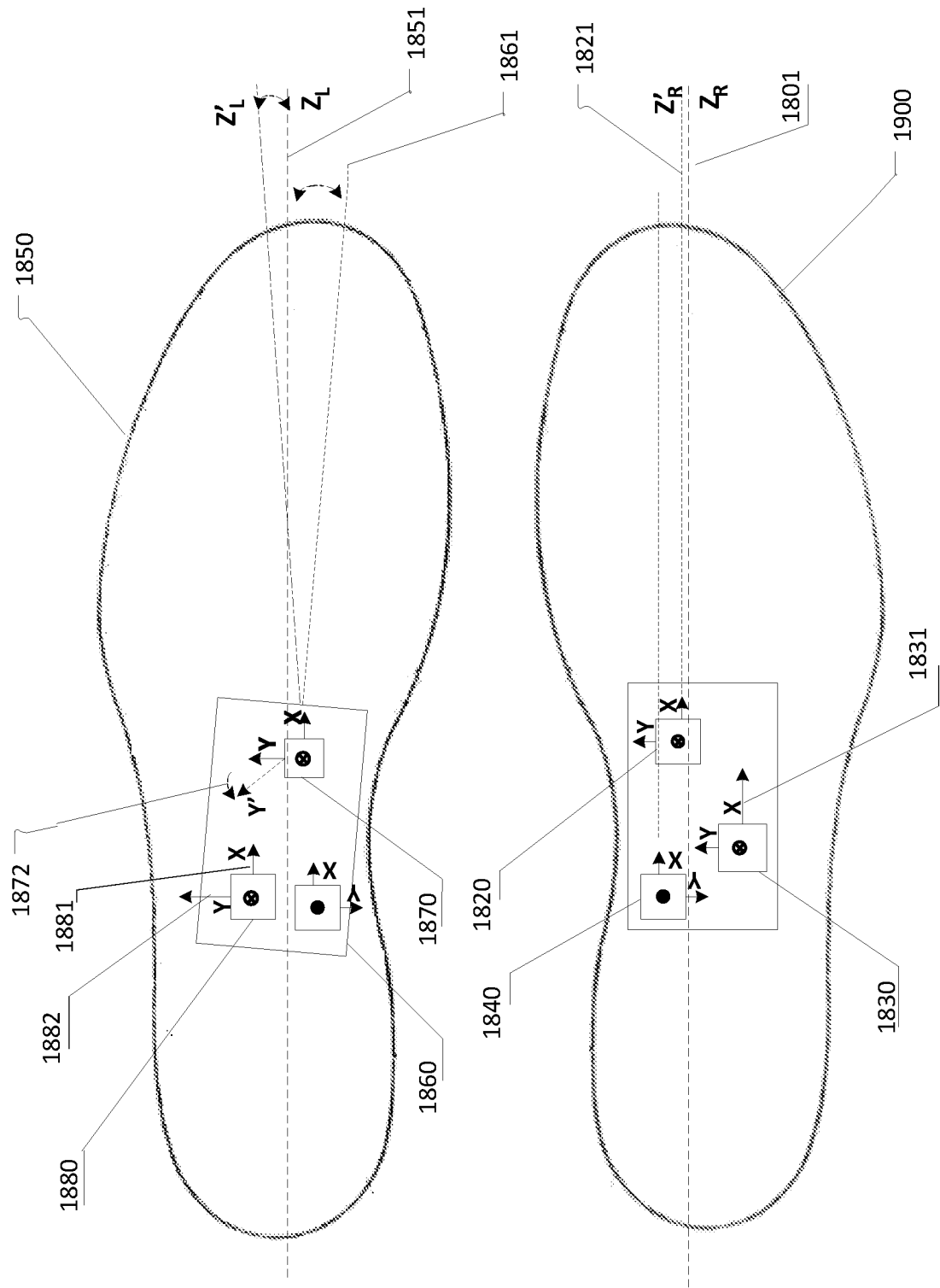
FIG. 18 presents an exemplary orientation of motion processing elements inside the footwear insoles.

For calibration purposes, assume that the individual motion processing elements are placed in the insoles as shown in FIG. 18, and that the insoles are placed on a flat, level surface (as if on a floor of a building) with the longitudinal axis of the insoles arranged approximately parallel to each other. By measuring the angles of the gravity vectors (as obtained from the x/y/z axis of the accelerometer), and by measuring the angles of the orientation vectors (as obtained from the x/y/z axis of the gyroscope), and assuming initial—uncalibrated matrices as shown in FIG. 8, and the previously defined matrix rotation term:

$$R_\theta = \begin{bmatrix} \cos\theta & -\sin\theta & 0 \\ \sin\theta & \cos\theta & 0 \\ 0 & 0 & 1 \end{bmatrix}$$

or the more elaborate equivalent:

$$\begin{pmatrix} r_{11} & r_{12} & r_{13} \\ r_{21} & r_{22} & r_{23} \\ r_{31} & r_{32} & r_{33} \end{pmatrix} \begin{pmatrix} v_x \\ v_y \\ v_z \end{pmatrix} = \begin{pmatrix} v'_x \\ v'_y \\ v'_z \end{pmatrix},$$

the relative orientation of the accelerometer and gyroscope can be obtained. Hence, the global and the local coordinate systems of the insoles can thereby be obtained, and the resulting matrix can be stored as an offset of the respective sensor. The offset can be used to rotate the matrix and hence have relation to the true orientation of the insoles. As the matrices are orthogonal with detriment "1", they can be transposed or inverse, and as such, we can reverse this rotation during the processing by multiplication with the matrix obtained from the samples of the respective sensor.

As described above in the description related to the processing of the user's motion, matrix operations are computationally intensive, especially when considering that such operations are performed for nine vectors received from each insole at the rate of between 100 to 200 times per second.

To avoid such intensive computations, the calibration offsets of the motion processing elements may be calculated after obtaining the global coordinate system by storing the difference between the magnitudes and the angles received from each respective axis of the three-axis accelerometer and the three-axis gyroscope. This is further described with reference to FIGS. 18, 19A and 19B.

FIG. 18 presents the left and right insole, where the right insole 1900, and the left insole 1850, are resting on a level surface with their longitudinal axis parallel to each other. For clarity of this exemplary description, assume that the right insole longitudinal axis $Z_R$ is aligned with the right insole motion processing element's gyroscope 1820, and that the right insole magnetometer's 1840, z-axis pointing upward and is denoted by a symbol •, and with the magnetometer z-axis at angle Ψ=0.00 degree, and the gyroscope 1820, z-axis $Z_R'$ 1821, parallel to the right insole axis $Z_R$ 1801, and the magnetometer x-axis pointing due North direction. Note, that z-axis of the gyroscopes 1820 and accelerometers 1830 are pointing downwards and are denoted by a symbol (arrow pointing down).

Furthermore, assume that the right insole accelerometer's x-axis does not record a value equal to 0.00 due to fabrication tolerances, or due to a slight misalignment in assembly (tilt along the y-axis), of the motion processing element inside the insole, or even that the entire insole is slightly pitching down (rotated along the accelerometer y-axis—pitched down). An effect of any of the above reasons is that the x-axis acceleration vector 1831 will be larger than 0.00. Such a hypothetical condition is represented here in form of the x-axis vector 1831 being longer than the accelerometer's y-axis vector.

For further illustration, assume that the longitudinal axis 1861 of the motion processing element 1860 of the left insole 1850 is misaligned in reference to the left insole longitudinal axis $Z_L$ 1851, with an angle Ψ>0.00. Assume further that the gyroscope 1870 is misaligned on the motion processing element PCB in such a way that the angle of the gyroscope z-axis $Z_L'$ is Ψ<0.00 in relation to the left insole $Z_L$ axis. Furthermore, due to the misalignments in the PCB soldering process, or due to the misalignment in the placement of the motion processing element inside the insole, or a misalignment of the insole inside the footwear, the y-axis 1872 of the left gyroscope 1870 is slightly tilted by an angle φ<0.00, while the vector of the accelerometer's 1880 x-axis 1881 is smaller than 0.00 and the accelerometer y-axis vector 1882 is larger than 0.00.

Figure 20:
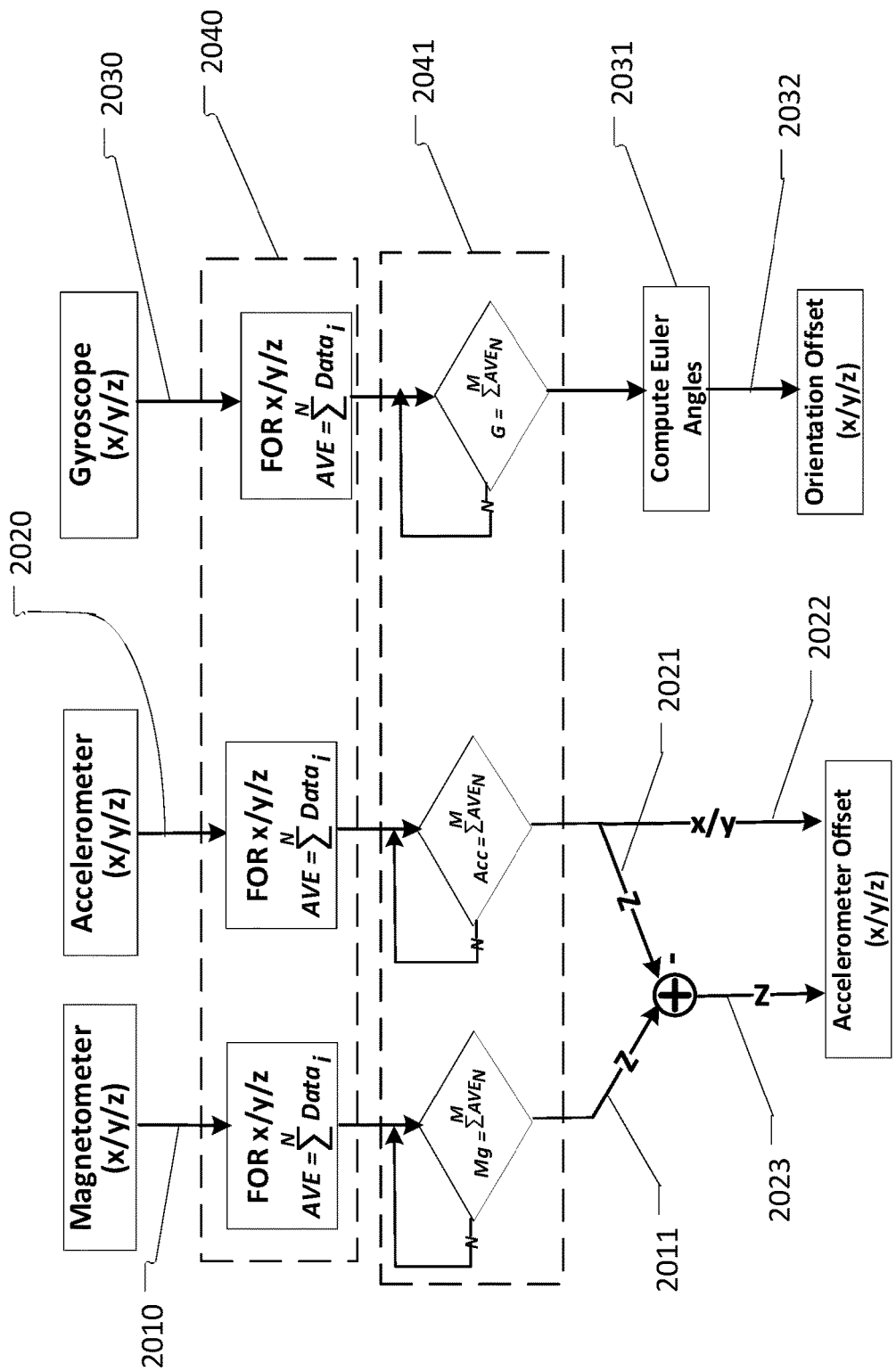
FIG. 20 is a flow diagram of an exemplary procedure for calibrating a motion processing element comprising a three-axis accelerometer, a three-axis gyroscope and a three-axis magnetometer.

Now, assuming that the orientation of the motion processing elements and the insoles are as described above with reference to FIG. 18, calibration of the motion processing elements embedded in the footwear or the insoles is described with reference to FIG. 20. To compensate for inaccuracies of the motion processing elements and to reduce variance of the references used as calibration values, several independent time averages of samples 2010 received from the magnetometer, samples 2020 received from the accelerometer, and samples 2030 received from the gyroscope, are averaged at a step 2040. This process is performed by first—averaging the samples 2010 received from the accelerometer, of N (for example where N=64), measurements of data received from each axis of each sensor, then preforming an average 2041, the result M times (for example, M=4), for a total average of M*N=4*64=256, thereby increasing the measurement signal-to-noise ratio (SNR) by approximately 24 dB. The advantage of taking a multiplicity of shorter, independent-in-time averages over the same length of a long term average, is evident to those skilled in the art. Assuming a measurement sample rate of 100 Hz, an average of 64 measurements will take approximately 640 milliseconds. Considering four such averages, separated by several milliseconds of idle time, the entire procedure will take less than 3 seconds to perform. After such averages are obtained for each of the three-axis of each motion processing element and each force sensor, the calibration values (or "calibration offsets") are obtained as follows:

FOR the x-axis and the y-axis of the accelerometer;
(a) obtain a data measurements from the x-axis and the y-axis of the accelerometer;
(b) record the data measurements as the calibration offset of the respective x and y axis 2022, of the accelerometer; and FOR the z-axis of the accelerometer:
(a) Obtain a data measurement from the z-axis 2021 of the accelerometer and from the z-axis 2011 of the magnetometer;
(b) subtract the value of data obtained from the magnetometer z-axis from the value of data obtained from the accelerometer z-axis; OR
(c) subtract the value of 0.98066 (an approximation of natural gravity), and store the result as calibration offset of the z-axis 2023, of the accelerometer;

FOR the data measurements obtained from the x, y and z axis of the gyroscope:
(a) compute the Euler angles 2031 for each respective axis of the gyroscope and record the results as the calibration offset 2032 of the respective axis of the gyroscope.

While the calibration procedure described above with reference to FIG. 20 provides calibration of the motion processing elements embedded in the insoles/footwear as shown in FIG. 18, it does not provide calibration of the plurality of the force sensors. While it is possible to calibrate the force sensors independently, one at a time using a known reference, such as, for example using a pressure press having a measurement capability, such calibration procedures are very time consuming. In contrast, in accordance with the present teachings, a calibration procedure may be performed using a single step that allows for joint calibration of both the motion processing elements and the plurality of force sensors. Such an exemplary procedure to calibrate for inaccuracies of the footwear or insoles only, or insoles in the footwear but without the effects induced by the user's weight and pronation is described now with reference to FIG. 21.

Figure 21:
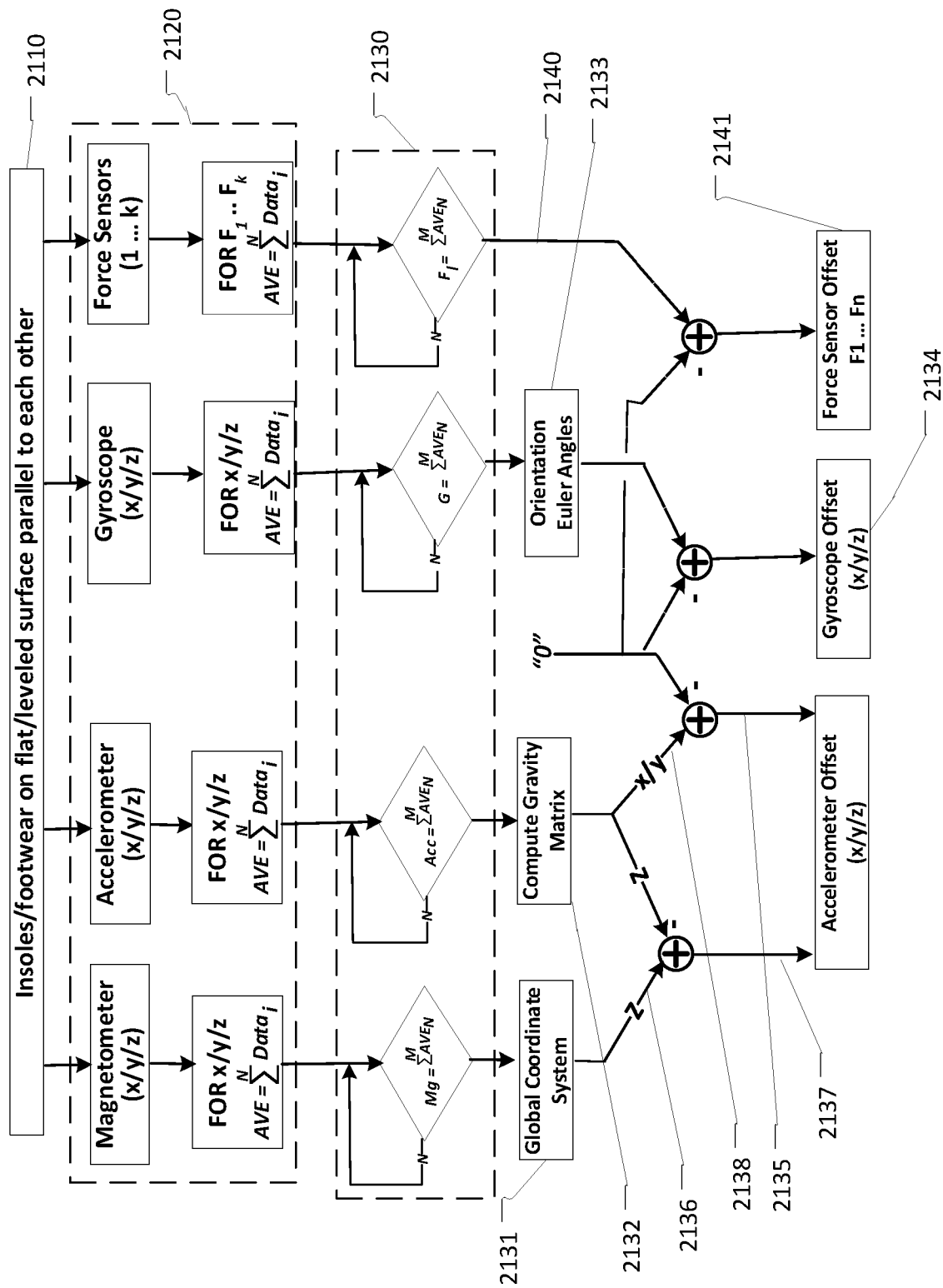
FIG. 21 is a flow diagram of an exemplary procedure for calibrating a motion processing element and force sensors, wherein the motion processing element comprises a three-axis accelerometer, a three-axis gyroscope and a three-axis magnetometer, and wherein the force sensors comprise a plurality of force sensors embedded in the footwear or within insoles embedded in the footwear.

First, the footwear/insoles are positioned on an approximately flat and level surface, with the footwear/insoles positioned approximately parallel to each other at a step 2110 as shown in FIG. 21;

For each insole:
(a) Obtain, several (independent in time) averages of the data measurements of the x, y and z-axis of the magnetometer, the x, y and z axis accelerometer, and the x, y and z axis gyroscope, by first, performing an average (at a step 2120) of N (for example N=64), measurements of data that are received from each axis of the motion processing element and from each force sensor, and then preforming an average (at a step 2130) of the result M times (for example, with M=4), and then:
i. using averages of the measurements of the Earth magnetic field obtained from the magnetometer, compute Global Coordinates at a step 2131;
ii. using averages of the measurements of the gravity vectors obtained from the accelerometer, compute a gravity field matrix at a step 2132;
iii. using averages of the orientation vectors obtained from the gyroscope, obtain insole/footwear orientation (Local Coordinates), by computing orientation Euler angles at a step 2133, then determine a gyroscope offset by subtracting a value of "0.00" from the Euler angle for each respective x, y and z-axis of the gyroscope and store the determined result as a calibration offset 2134 of the respective x, y, and z-axis of the gyroscope;
iv. using averages of the gravity vectors of the x and y-axis (arrow 2138 in FIG. 21), of the accelerometer obtained during computation of the gravity filed matrix, compute the calibration offset 2135 of the x and y-axis of the accelerometer by subtracting the value of "0.00";
v. using averages of the gravity vectors of the z-axis of the accelerometer obtained during computation of the gravity field matrix, compute the calibration offset 2137 of the z-axis of the accelerometer by subtracting the value of the z-axis 2136 (natural gravity) obtained from the value of the z-axis of the magnetometer obtained during the computation of the Global Coordinate System at step 2131;
OR
by subtracting the value of "0.98" from the measurement of the average of the gravity vectors of the z-axis of the accelerometer obtained during computation of the gravity matrix 2132;
vi. using averages of the force sensors measurements 2140, subtract the value of "0.00", and record the results as a calibration offset 2141 of the respective force sensor;
vii. without changing of the footwear/insole position, verify the calibration procedure by:
(b) Obtain several independent in time 2130 averages of the data measurements 2120 of data measurements received from the accelerometer, the gyroscope, and from each of the plurality of force sensors, then;
i. subtract the respective calibration offsets of each respective axis of the accelerometer and the gyroscope then verify:
FOR the accelerometer x-axis, and y-axis the result is approximately equal to 0.00, and for the accelerometer z-axis, the result is approximately equal to 0.98;
FOR the gyroscope x, y and z-axis the result is approximately equal to 0.00; and that the result of the heading of the right and left insole/footwear is approximately equal to 0.00; and
ii. subtract the respective calibration offsets of each respective force sensor from the average measurements received from the respective force sensor and verify that the results are equal to approximately 0.00.

During processing of data measurements received from the insoles, the calibration offsets of the respective axis of the respective sensor calculated above are subtracted from (or added to) each data measurement obtained from the respective axis of the respective sensor. For example, the calibration offset of the accelerometer x-axis is subtracted from the x-axis data measurements received from the accelerometer. Similarly, the calibration offset of the accelerometer y-axis is subtracted from the y-axis data measurements received from the accelerometer. Similarly, the calibration offset of the accelerometer z-axis is subtracted from the z-axis data measurements received from the accelerometer. Likewise, the calibration offset of the gyroscope x-axis is subtracted from the x-axis data measurements received from the gyroscope. The calibration offset of the gyroscope y-axis is subtracted from the y-axis data measurements received from the gyroscope. Finally, the calibration offset of the gyroscope z-axis is subtracted from the z-axis data measurements received from the gyroscope.

While the above procedure provides accurate calibration of the insole/footwear orientation and force sensors, it does not compensate for inaccuracies introduced by the user's physical characteristics, such as, for example: natural pronation (over-pronation, supination), body weight and body weight distribution, associated distribution of the GRF, location of the center of balance (POB) and center of pressure (COP). In order to provide correct analysis of the user's motion, it is necessary take into the account the user's physical characteristics. To that end, a calibration may be performed similar to the calibration method described above and also taking into account the joint characteristics of the insole/footwear plus the user, or use the previously described calibration method as a step 1 to establishing footwear reference, then in step 2 performing a joint calibration with the user's wearing the footwear and storing the difference between step 1 and step 2 as the user's physiological characteristics—natural pronation; body weight distribution, location of the POB and the COP. The fundamentals of this calibration method is described with reference to FIGS. 19A and 19B, and then the actual calibration procedure is described.

The user's balance (or motion), is analyzed in reference to the vertical ground reaction force (GRF) applied by the user's foot at the points of balance (POB)—namely: the 1st MT, the 5th MT and the heel, as more than 95% of the user's body weight is transmitted through those points to the ground. As described above, the values of the GRF are measured using, for example, suitable resistive or capacitive pressure sensors embedded in the insoles under the user's 1st MT, the 5th MT and the heel of the foot.

Figure 19A:
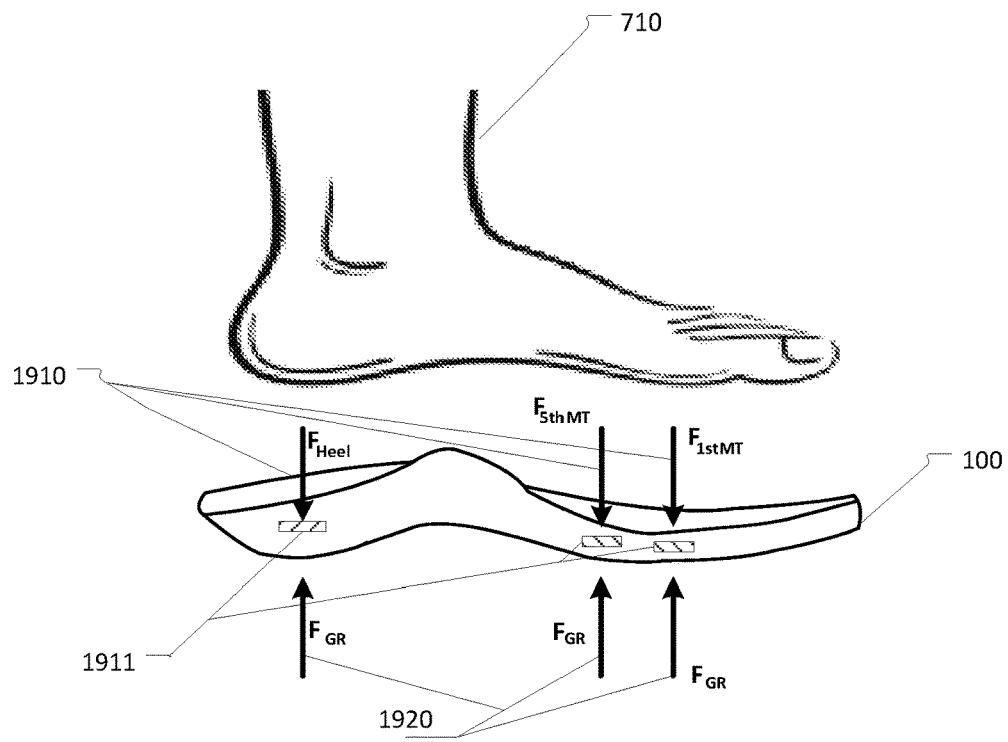
FIG. 19A presents relation between pressure points of a user foot and the ground reaction forces as measured by the pressure sensors.

It is well known that force equals the mass of an object multiplied by the acceleration (F=m*a), and is measured in the units of Newton (N), where 1N=1 kg*1 m/sec$^2$. It is assumed that the gravity vector g=0.9806.65, and the force of 1N=0.102 kg*9.80665 m/s$^2$. Therefore, pressure induced by the user's weight is recorded as force. If this force is applied perpendicularly to the surface of an object, this force is referenced in relation to area over which that force is distributed and is as defined in dimensional analysis as F=ML/T$^2$; where M is mass, L is length and T is time. FIG. 19A shows a relation between the user's body weight represented by the foot, and forces applied to the user's POB (where F=the user's weight/3*9.80665 m/s$^2$), as $F_{1stMT}$; $F_{5thMT}$; and $F_{Heel}$. This is directly opposite and equal to the GRF 1920, which are measured by the plurality of force sensors 1911 that are embedded in the insole 100. Assuming perfect balance, the user's foot 710 represents ½ of the user's weight and is represented as an equal force 1910, distributed between three sensors, that is applied to the user's point of balance—namely the 1st MT, the 5th MT and the heel of each foot. Said forces cause a reactional force from the ground, which is equal to the force (Newton's 3rd Law).

Assuming the user is standing in a natural position with the user's body relaxed, and with the user's feet shoulder width apart, and with the user's toes pointing straight ahead, each of the pressure sensors shall record force equal to:

½User_body_weight[kg]*0.102*9.80665[N], normalized by the number of sensors.
This property and knowledge of the user's weight—included in the first information is used in calibration and processing of data received from the force sensors.

Figure 19B:
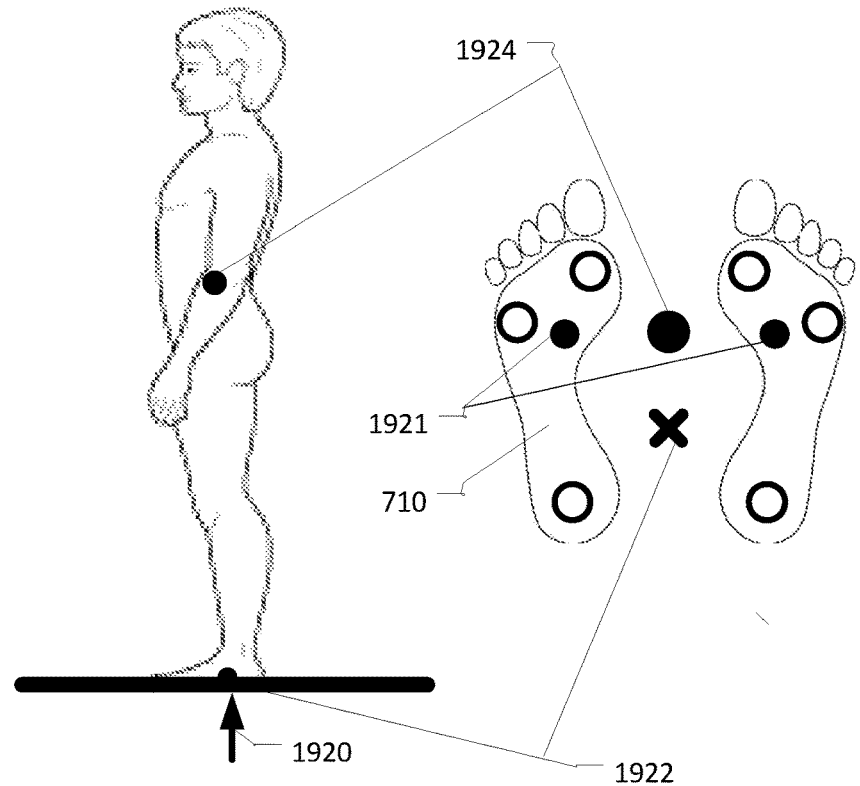
FIG. 19B presents relation of the user's body position in relation to the distribution of GRF at the feet POB and location of COP and COM.

This calibration technique is described with reference to FIG. 19B. Here, the user with neutral pronation, stands in a natural position, with feet positioned at a shoulder's width apart from one another and with body weight equally distributed between both feet. In this position, the vertical GRF 1920 is evenly distributed between the left and the right foot and the feet COP 1921, is positioned between the 2nd and 3rd Metatarsal and arch of each foot 710, while the body COP 1922, and the user's center of weight is positioned between the user's feet and below the COM 1924.

Assuming such position and assuming that the user has a neutral pronation, each force sensor shall record ½ of the user's body weight normalized by the number of sensors, and the GRF present at the foot COP will equal the following:

$$F_{GRF}=F_{1MT}+F_{5MT}+F_{Heel}$$

The location of the foot COP can be obtained in 2D Euclidean space using Cartesian coordinates of the POB location, or by computation of a weighted average of the forces. Similarly, by computing the ratio of GRF present at each foot, the body weight distribution can be determined, and the location of the user's body center of mass can be computed, which is the 1st moment of mass normalized by the total mass: R=1/M Σri mi; where mi is the number of points (sensors) over which the user's body mass is distributed. Such measurement aids in determination of the user's physiological condition—such as: abnormal distribution of the body weight between the user's feet due to a limp, injury or other physical conditions, etc. This information may aid in an analysis of progress in the user's recoalescence, providing corrective feedback, etc.

A user with overpronation will roll his or her foot inward, placing more of the user's body weight on the 1st MT, while a user with supination, will roll his or her foot outward and will therefore place more of the user's body weight on the 5th MT. In both the overpronation and supination cases, the total GRF will still be ½ of the user's body weight [kg] *0.102*9.80665 [N], unless, the user's center of mass is significantly shifted sideways, which case can be determined using the computation described in the previous paragraph.

It is evident that if the user's natural pronation is not taken into account during calibration, a simple calibration of the force sensors such as the calibration procedure described above produces errors for users with overpronation or supination. However, as the footwear has been independently calibrated as described above without taking the user's natural pronation into account, it is possible to detect such conditions and adjust the calibration data accordingly. While detection of overpronation or supination is desirable, consideration of such conditions on the actual calibration of force sensors should be considered. This is important, because, for example, a user with supination will place more of his or her mass on the 5th MT rather than on the 1st MT, due to the fact that the total GRF measured at the user foot POB is distributed between the 1st MT, 5th MT and the heel. Assume that a user's foot of a person with supination rolls outward by several degrees. This will cause a shift of the mass applied to the 5th MT of the user's foot to move sideways, effectively causing a lateral force, and a moment proportional to the mass and distance of the displacement. This moment is a product of the force (F) and the distance (r), as: M=F*r, wherein the distance is provided by measurements received from the accelerometer, and the angular relation of the acceleration vector—obtained from the gyroscope, is referred as a moment of inertia, and determines the force of acceleration. The knowledge of such moments lateral (and horizontal) components of the GRF when obtained during calibration aid in determination of abnormal foot conditions, recoalescence from leg injuries, or in providing a corrective feedback.

This calibration method is accomplished by:
a) determining overpronation or supination by observing the angle of rotation along the gyroscope x-axis;

b) calculating a moment present at the 1st MT (overpronation), or the 5th MT (supination) using well known formula M=r*F, where r is given by the magnitude of the accelerometer y-axis. Or, taking into account the angular relation between distance and force, computing a center of mass (body or foot), the 1st moment of momentum, or computing a moment of inertia, the 2nd moment of mass;

c) adding or subtracting the result from the calibration offset of the respective force sensor.

Figure 22:
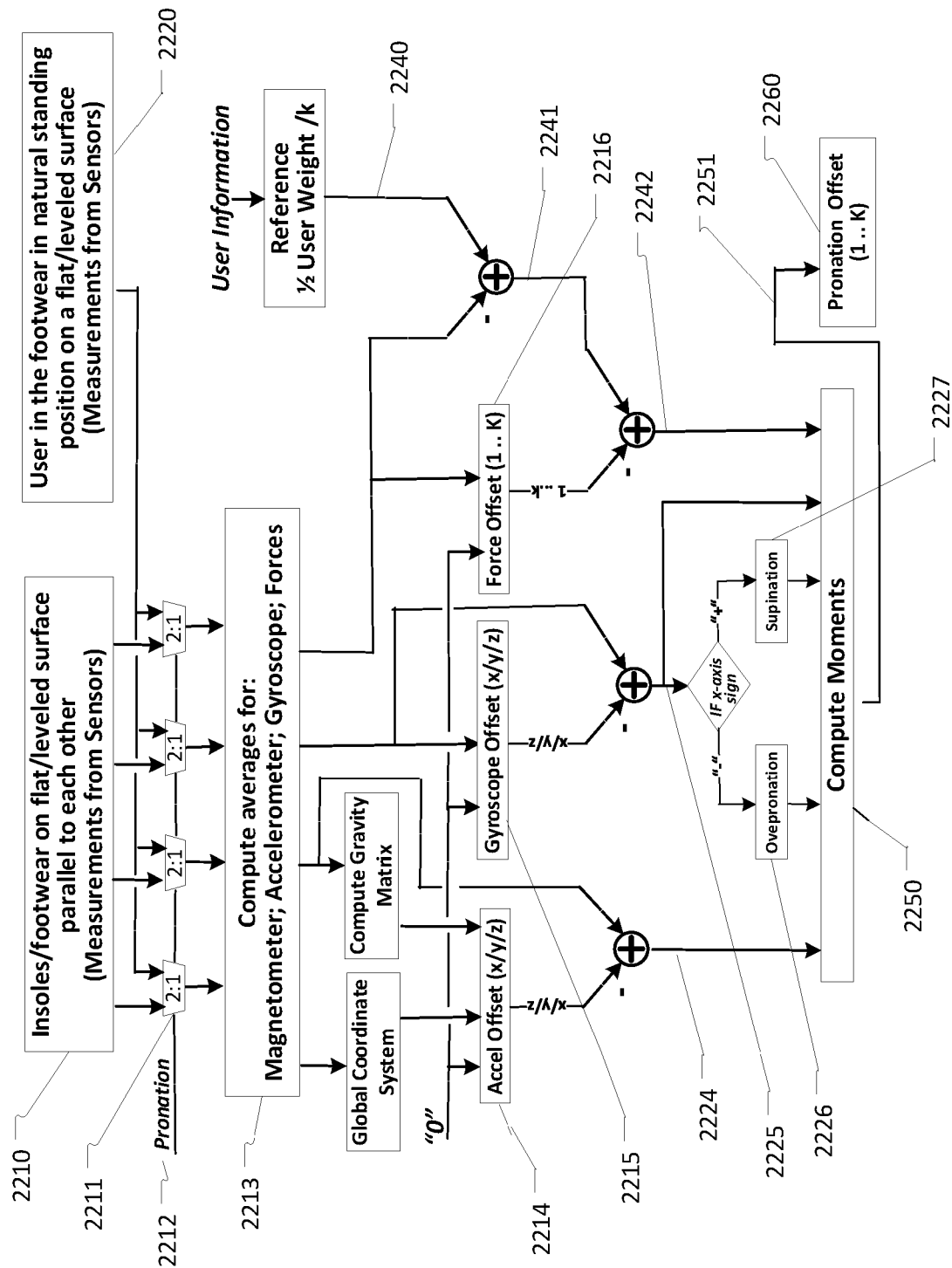
FIG. 22 shows a calibration procedure which performs calibration of a motion processing element and force sensors; wherein the motion processing element comprises a three-axis accelerometer, a three-axis gyroscope and a three-axis magnetometer, and wherein the force sensors comprise a plurality of force sensors embedded in the footwear or within insoles embedded in the footwear. The procedure also performs calibration of the motion processing element and force sensors taking a user's natural pronation into account.

This calibration process is described with reference to FIG. 22. To obtain calibration of the motion processing elements and the plurality of force sensors, and the user's pronation characteristics, the motion processing elements and force sensors should in most cases first be calibrated independent of the user's pronation characteristics. This independent calibration of the motion processing elements and the plurality of force sensors is described above with reference to FIG. 21. After performing the independent calibration procedure described above with reference to FIG. 21, a joint calibration technique may be performed for the insoles/footwear and taking into account the user's physical pronation and weight characteristics, with the difference recorded as the pronation calibration offsets. Those of skill in the art shall appreciate that such calibration procedures have several advantages: from such trivial advantages as aiding in a selection of an appropriate user insoles/footwear, to the manufacturing of custom footwear, an analysis of foot disorders, post injury recovery solutions, etc. During calibration of the footwear calibration reference, footwear without the user's feet are placed on a flat level surface, positioned approximately parallel to each other at a step 2210 (see FIG. 22). A pronation signal 2212, is set to "inactive". This allows obtaining of measurements from the insoles without distortion caused by the user's pronation and weight. Several (independent in time) averages of the data measurements of the x, y and z-axis of the magnetometer, the accelerometer, and the gyroscope and the plurality of force sensors are determined at a step 2213. A Global Coordinate system and gravity measurements are obtained, and the footwear-only calibration offsets of the accelerometer (at a step 2214), the gyroscope (at a step 2215) and the plurality of force sensors (at a step 2216) are obtained.

In a following procedure, calibration, taking into account the user's natural pronation, is obtained. In accordance with this procedure, the signal "Pronation" 2212, is set to "active", and the user is instructed to step into the footwear and stand in a natural relaxed position with feet approximately a shoulder's width apart from one another (see a step 2220 in FIG. 22). Several (independent in time) averages of the data measurements of the x, y and z-axis of the magnetometer, the accelerometer, and the gyroscope and the plurality of force sensors are performed at a step 2213. A pronation gravity offset 2224 is computed by subtracting the accelerometer offsets 2214 from the averages 2213, of the current measurements received from the accelerometer. Similarly, the gyroscope offsets 2215 are subtracted from the Euler angles computed from the average 2213, of the current measurements received from the gyroscope, and if the sign of the result is "−" (minus), the result 2225 is recorded as overpronation at step 2226. If the sign of the result 2225 is positive "+" (i.e., plus), the result 2225 is recorded as "supination" at a step 2227.

To calibrate the effect of the user's weight and pronation on the measurements of the force sensors the following technique is performed. The user's weight (obtained from the first information) is divided by two, then the result is further normalized by the number of force sensors embedded in each footwear (the user's weight is equally distributed between the user's feet and between each force sensor (in one example it is: User's_weight/6), (see block 2240 in FIG. 22). The averages computed in the step 2213 are then subtracted from the current data measurements received from each force sensor and from the normalized user's weight (2240). The result of this operation 2241 is further subtracted from the force sensor offsets 2216, and the difference (2242) if any exist, (caused by unequal distribution of the user's weight over the user's foot POB due to overpronation)—more pressure on the 5th MT, and supination—more pressure on the 1st MT.

With overpronation or supination, the GRF present on the 1st MT and the 5th MT have a lateral component in addition to a vertical component. As such, the resultant force shifts the center of mass sideways, creating a moment of force, while the measurements received from the force sensors are either under-valued or over-valued. Taking advantage of the previously calculated angles of the over or under pronation, the actual moments 2250 are calculated, produced by the resultant GRF. This calculation is performed in order to avoid non-linearity of simple addition/subtraction, and to compute the force sensors pronation offsets. The force sensors pronation offsets are obtained as follows:

Using the magnitude of the y-axis vector 2240, of the accelerometer as a displacement of a location of mass of the user's foot r, and the results of the subtracting of the force sensor offset 2216 and the normalized user mass (2241) as F (force), compute the moment 2250 present at the center of the MT as: M=r*F, then compute the resulting force component 2251, as F=M/r and store the result as the respective force sensor pronation calibration offset 2260.

As a result of this calibration method, all fabrication and assembly tolerances and errors can be compensated for by subtracting the relevant calibration offsets from each data measurement received from each motion processing element and from each of the plurality of force sensors. The current footwear/foot orientation using the Euler angles (or from the rotation matrix, or from the quaternion), in form of pitch (rotation along y-axis), roll (rotation along the x-axis), and heading direction (rotation along the z-axis). Similarly, after correcting for the fabrication and assembly errors, using the three-axis accelerometer results, we compute the g-force applied to each foot by algebraically squaring values of the x, and the z-axis, and subtracting the Earth natural gravity.

After power ON, the MCU 1034, enters standby mode and remains in said mode until an interrupt from the insole pressure sensor exceeds a threshold pTh_1, indicating that both of user's feet are in the ski boot and on the ground. If a new calibration is not required, the system enters normal operation. As shown in FIG. 12, at Step 1, the global and local coordinate systems are obtained, and the method then enters the Step 2. In Step 2, the system starts monitoring motion, and if the velocity exceeds a threshold vTh_1 indicating a start of a run, the system enters Step 3, whereat the motion processing element and force sensor data are transmitted to the smart-phone application via the radio interface 211. System remains in State 3, until the velocity falls below a threshold vTh_2 and the pressure force measurement falls below a threshold pTh_2. When the velocity is below the threshold vTh_2 and the pressure forces is below the threshold pTh_2, indicating end of day (ski boot off), or time-brake in skiing (lift, rest, etc.), the system enters a Step 4, stops processing the motion and force data measurements, forces the radio interface transceiver 1036 into a power OFF mode and the MCU 1034 into a standby mode, thereby conserving power consumption of the system. After exiting the Step 4, the system remains in the sleep mode until condition of Step 2—pressure force above pTh_1 and velocity above vTh_1 conditions are not satisfied.

The motion and pressure force data received from the insole 100, by the smart-phone 200, is processed by application 300 to provide user with the haptic feedback. Based on signal from sensors, using inertia navigation algorithms, application calculates kinematics of the ski trajectory. Then using user parameters, creates biomechanical model of foot/ski interface, and the sensor kinematics is translated to segments kinematics by measuring the position (and timing) of COF. Such calculation provides two results: one, current ski trajectory; two, prediction of future trajectory in relation to the local coordinate system and location of COF. The first set of results are sent to the cloud based server 500 for further processing using smart-phone cellular radio interface 221, while the second sets of results is used to provide corrective feedback to the user foot.

This corrective feedback is in form of haptic pulses applied by the haptic actuator to the big toe of the foot. This feedback provides information of timing, direction and destination of the COF necessary to successfully start and finish turn. This feedback may be coded in various ways, for example, different frequency and/or force during different phases on turn, etc.

Figure 17:
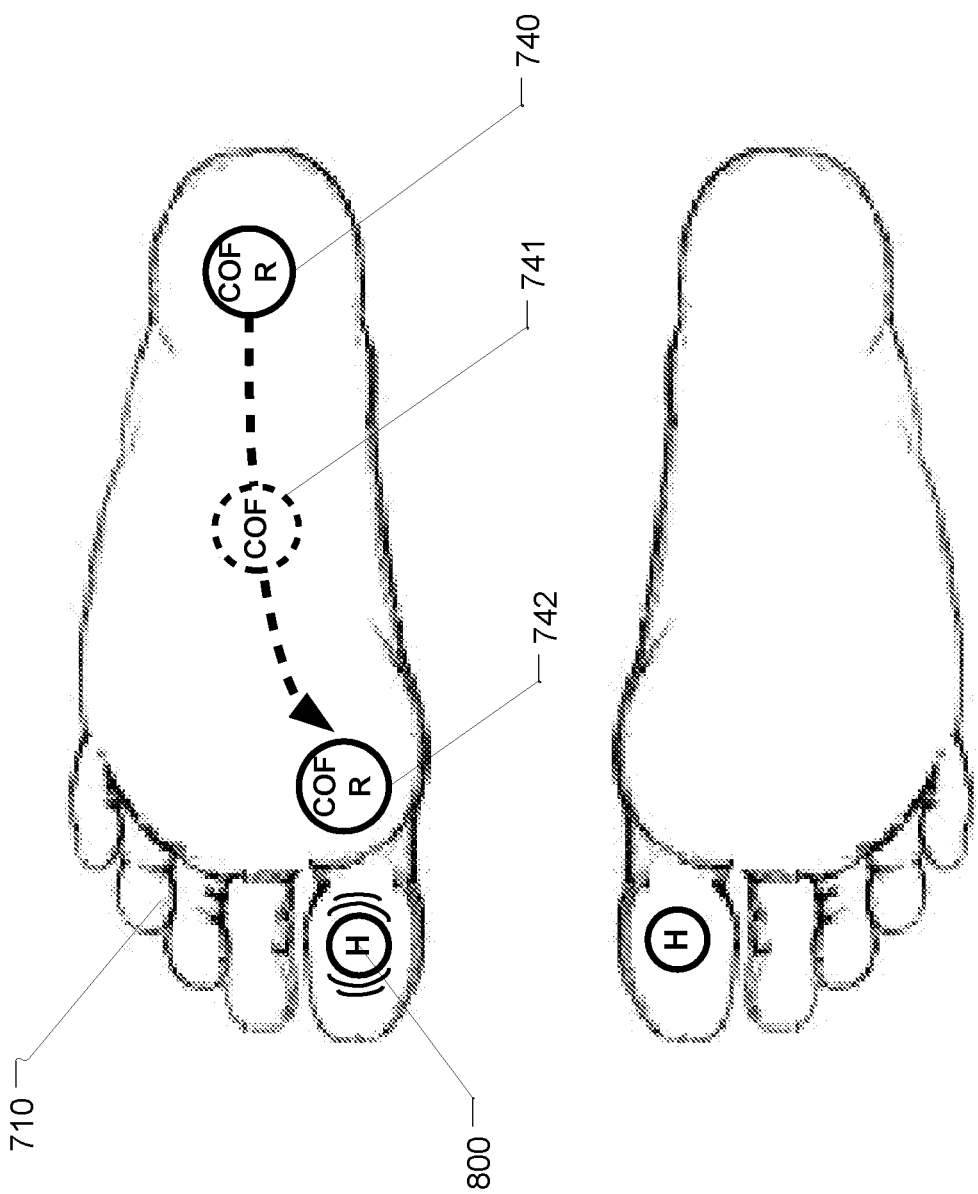
FIG. 17 presents operation of haptic feedback actuator on the outside foot during the transition into left turn.

Operation of said haptic feedback is presented in FIG. 17. Here we see the outside (of the turn) foot 710, right after start of transition, which the haptic feedback actuator 800, vibrating at high frequency (or force), when the COF is still located under skier heel, indicating time to transition on the outside ski and move COF to the base of 1st MT. The vibration frequency may decrease while COF moves forward to new position 741, and completely stop when the COF reaches the desired position 742, while never stop vibrating at high frequency when the COF fails to reach the base of 1st MT.

Together with the first set of results, application sends to the cloud server GPS coordinates and timing. The first set of data is then used to generate a numerical and graphical presentation of the run. An exemplary representation of run data is presented in FIGS. 14, 15 and 16. Such run data may be retrieved form the cloud server later by the user and displayed on the user smart-phone (for example during the travel on the lift), or in real-time on a remote computer. Furthermore, using the GPS coordinates, cloud server may superimpose said data on 3D map of the terrain, giving additional reference and meaning to the data.

Figure 14:
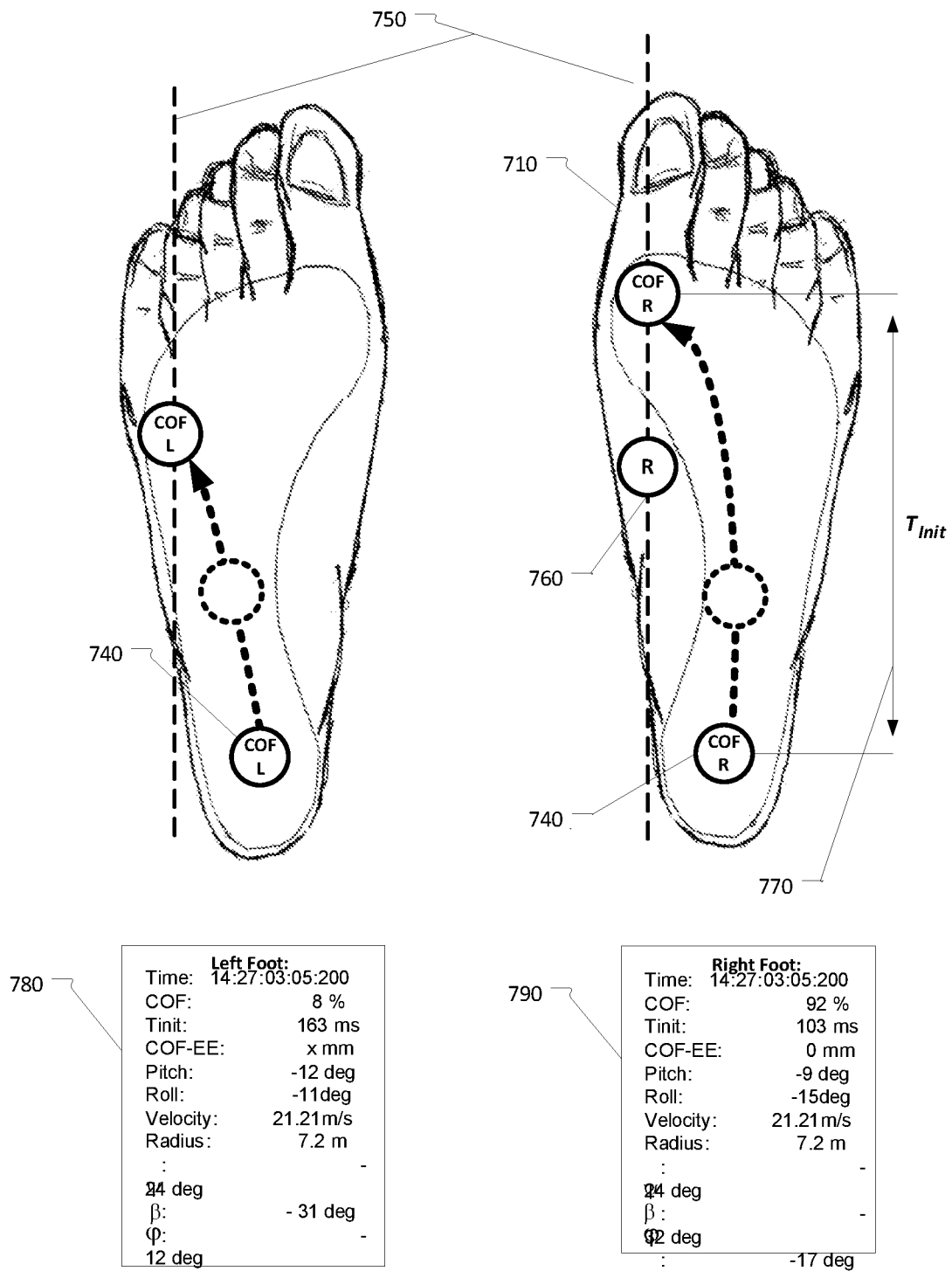
FIG. 14 presents graphical and numerical representation of motion and pressure points transmitted to the ski boot insole by the foot during a successful turn.

After the post-processing of first set of results by the remote cloud server, visual and numerical representation of the run can be displayed on a remote computer or on a smart-phone. Among the others visual presentation possible, some of the visual options are presented in FIGS. 14, 15 and 16. FIG. 14 shows left and right foot with a graphical representation of the location of COF and 3D motion parameters in relation to the GPS time. Here we see the movement of the COF 740 from the start of transition into the left turn, the location of the COF 742 after the initial phase of the turn and the time (in milliseconds), of the transition 770. Furthermore, the calculated location of the resulting force FR 760, a point where the skier center of mass (COM) is acting on the ski and snow.

Figure 15:
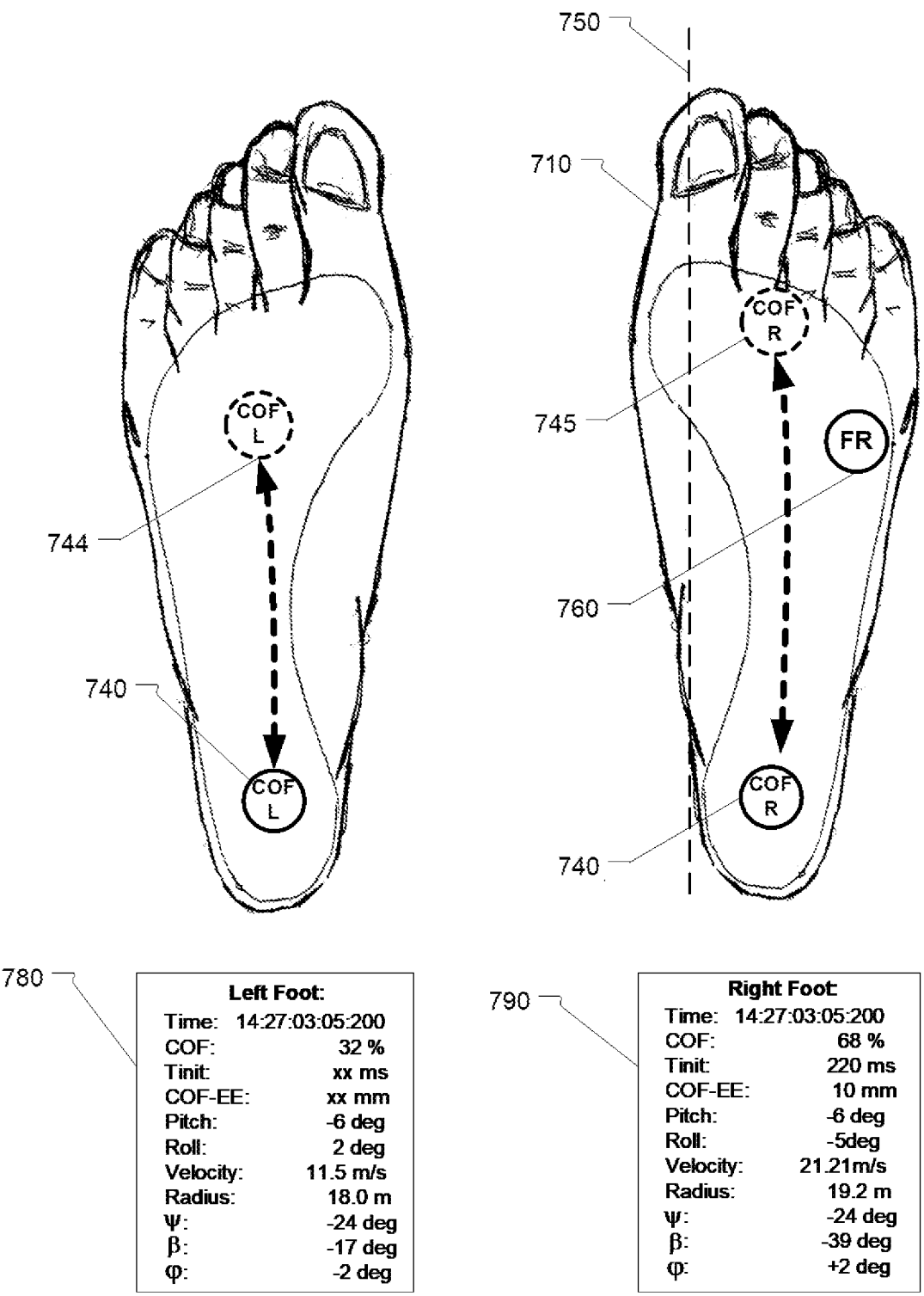
FIG. 15 presents graphical and numerical representation of motion and pressure points transmitted to the ski boot insole by the foot during an unsuccessful turn.

The graphical and numerical results, representing unsuccessful turn is presented in FIG. 15. Here we see the mistake user makes during the start of transition (flat ski=>select new ski=>COF of inner foot to head of 5th MT), inner foot COF forward to the center of foot 744. In order to maintain balance, the COF of the outer foot was placed between the 2nd and 3rd MT 745, and the resulting force moved to the outer edge of the outer foot. In this position the body kinematics does not allow for pelvic rotation and in effect, the COF return to the heels of the feet—balance is lost, turn can't be finished until balance is recovered during next flat ski.

Data are analyzed in relation to velocity, pitch and roll and effective radius of the turn and other numerical results 780 and 790 for left/right foot respectively and may be used by both the amateurs to improve their skills, professionals during training, judges in analyzing performance of a free style or figure skating competition or even commentators during televised sports events. Furthermore, those results may be sorted and presented in various statistical formats selected by the viewer. An example of such statistical analysis may be use in training and evaluation of turn symmetry—one of most important parameter of measuring progress of a professional skier. Turn symmetry, is term used to describe a pressure applied during the left and right turn. The closer is the distribution of pressures between inner/outer ski during the left and right turns, the better will the skier perform. Such analysis is currently limited to visual observation by the coach of the racer during a run over a specific part of the slope where the transversal angle of the slope maintains relatively constant angle to the line of the slope. Such observation is subjective, prone to errors and of limited value—as it's impossible to evaluate the symmetry of pressure visually and specifically on the slope with changing topographical parameters.

Turn symmetry statistics can be performed as follows:
(a) Log all left turns into LEFT SET, and all right turns into RIGHT SET;
(b) FOR each turn with $\phi_L=\phi_R$ OR $-\phi_L=+\phi_R$ OR $+\phi_L=-\phi_R$ (roll):
  (i) Extract pressure points and force data;
  (ii) Sort pressure points and force data in the descending order of difference. Similar method may be used for numerous other parameters of the run.

Figure 16:
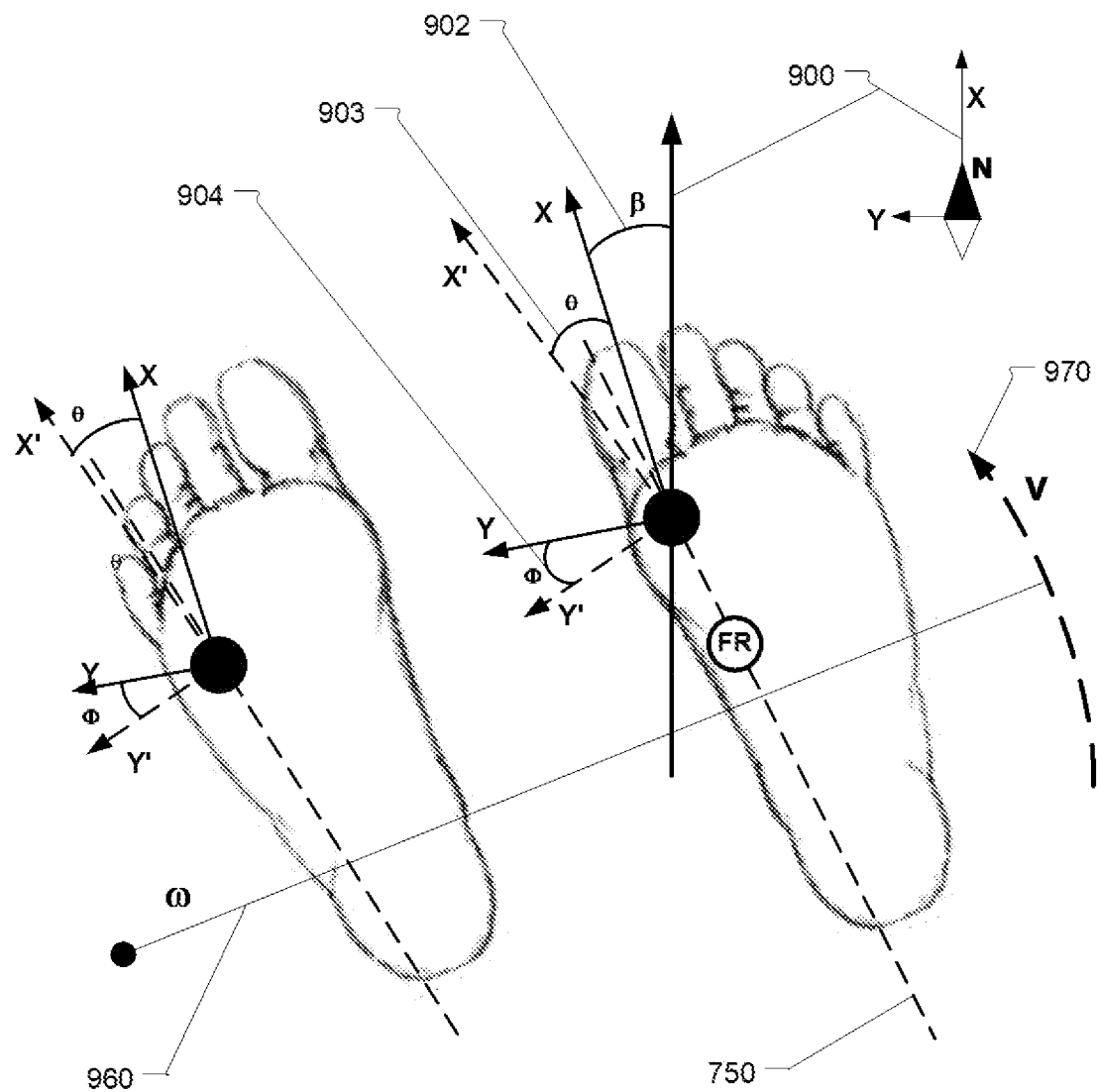
FIG. 16 presents another version of graphical representation of motion in relation to the pressure points on the ski boot insole.

Different view of the data presented in FIG. 16, where both feet are shown in relation to the global coordinate 900, the angle β, 902 to the local coordinate X, pitch ⊖, 903, of the ski (angle between X and X)', the roll inside the turn ϕ, 904, the effective turning radius ω, 960, and velocity V 970. The location of resulting force $F_R$ in relation to the ski edge 750 is also presented.

Another embodiment of feedback system may employ direct control by an instructor of coach. Here, motion and force sensors data is relayed by the smart-phone 200, to the remote device 700, operated by instructor or coach, who maintains visual contact with the user. On the device 700, data is processed by application 300, enhanced with a user interface (UI), allowing to manually control the haptic feedback actuator embedded in the user ski boot insole. The input from the terminal 700, UI operated by instructor, is send back over wireless cellular interface 400 and 221, to the user smart-phone 200 and then using the PAN wireless interface 210 to the haptic feedback actuator 1033, located in insole 100. Such embodiment allows the couch to directly influence the user actions and tailor his training/progress according to predefined plan or changing slope conditions.

In some embodiments, the force sensors can be calibrated or recalibrated one or more times while the user has his/her feet on the insoles, such as while the user is skiing, riding in a ski lift, etc. For example, the force sensors can be recalibrated on a repeated basis while the user is skiing (e.g., with his/her feet on the insoles). Recalibrating the force sensors can reduce force measurement errors that can occur such as due to drift and/or temperature changes.

The repeated basis can be a periodic basis in which recalibration can occur at least once every force recalibration period. The force recalibration period can range from every 15 seconds to every 60 seconds, including every 30 seconds, every 45 second, and/or any other value or range between any two of the foregoing time periods. In some embodiments, the force recalibration period can be less than or equal to every 15 seconds (e.g., every 5 seconds to every 15 seconds). Additionally or alternatively, the force recalibration period can be greater than or equal to every 60 seconds (e.g., every 60 seconds to every 90 seconds). In some embodiments, the force recalibration period can be based, solely or partially, on a predetermined number of ski turns.

Calibration and recalibration generally refer to the same method, process, and/or system and can be used interchangeably. Calibration and/or recalibration can be controlled by the application running on the mobile terminal, such as by sending control signals to the force sensors (e.g., via Bluetooth transceivers or other radio transceivers) and receiving/obtaining data measurements from the force sensors.

In another example, the force sensors can be recalibrated on an irregular basis and/or variable time basis. In another example, the force sensors can be recalibrated when or after a force recalibration event is detected. Examples of a force recalibration event include (a) a temperature change above a maximum value compared to the temperature at which the force sensors were calibrated most recently; (b) the elapsed time since the force sensors were calibrated most recently is greater than a maximum value (e.g., ranging from 5 minutes to 7 days); (c) the detection that the user has begun to ski (e.g., as opposed to taking a break during a ski run, riding in a ski lift, etc.); (d) the detection that the user has completed a ski turn or a predetermined number of ski turns; and/or (e) the receipt of a manual recalibration request from the skier (e.g., via the skier's smartphone, a recalibration button, etc.). The temperature change can be a change in temperature of the outside temperature (e.g., as measured by a temperature sensor on the skier or his/her equipment) and/or a change in temperature of the force sensors (e.g., as measured by a temperature sensor on or proximal to the force sensors, such as on the insole).

The Recalibration of the Force Sensors can Include the Following Steps:

For each sensor in each insole:

(a) Obtain and/or record several data measurements at a sampling rate (e.g., a predetermined sampling rate) from the force sensor over a time period. The time period can be a predetermined time period. In some embodiments, the predetermined time period is the same as the force recalibration period. For example, when the force recalibration period is every 30 seconds, data measurements from the force sensor are taken over 30 seconds at the predetermined sampling rate. In another embodiment, the predetermined time period is different than the force recalibration period. For example, when the force recalibration period is every 30 seconds, data measurements from the force sensor are taken over 20 seconds at a predetermined sampling rate, such as by excluding the first 5 seconds and the last 5 seconds of the 30 second force recalibration period. The length of the predetermined time period can be selected such that, on average, the skier will make at least one ski turn during the predetermined time period. As such, the data measurements for the force sensors in each insole can include peak values that correspond to the use of the respective foot as the downhill ski to make a turn in the opposite direction (e.g., the left foot is used as the downhill ski when making a right turn). In addition, the data measurements for the force sensors in each insole can include minimum values that correspond to the use of the respective foot as the uphill ski when making a turn in the same direction (e.g., the right foot is used as the uphill ski when making a right turn).

In the embodiments where the force sensors are recalibrated on an irregular basis, on a variable time basis, or in response to the detection of a force recalibration event, the predetermined time period can vary between every 15 seconds and every 60 minutes and/or any value or range between any two of the foregoing values, or may not be predetermined at all. The predetermined time period can be less than or equal to 15 seconds or greater than or equal to 60 minutes. When the time period is not predetermined, the duration can be dictated by external events, such as the duration of a detected ski turn. Alternatively, the predetermined time window can be replaced by a predetermined number of detected turns (e.g., a predetermined ski-turn window), so as an example, data from the previous 5 turns will be used for calibration.

In some embodiments, the data available for calibration may only include the data when skiing is detected. As an example, if the predetermined time window is set to 30 seconds and the user has recorded a first ski run, taken a lift and is now 15 seconds into a second ski run, the data used for calibration will consist of the last 15 seconds of the first ski run and the first 15 seconds of the second ski run. Alternatively, the calibration routine may only use data from within the same ski run.

In some embodiments, the data available for calibration may only include the data obtained while the user is making a ski turn. In some embodiments, the data available for calibration may only include the data obtained while the user is making a ski turn and a time period before the start of the ski turn. The time period before the start of the ski turn can be set or predetermined. Examples of the time period before the start of the ski turn that can used for calibration can be within the range of 10 seconds to 60 seconds before the start of the ski run, including 20 seconds, 30 seconds, 40 seconds, and 50 seconds, and any value or range between any two of the foregoing times. In other example, the time period before the start of the ski turn that can used for calibration can be lower than 10 seconds and/or higher than 60 seconds.

(b) Determine the force calibration offset using the data measurements from the time period. The force calibration offset can be determined based on one or more statistics of the data measurements. For example, the statistic(s) can include the minimum, maximum, average, median or any percentile, such as the 1st or 5th percentile, and/or another statistic. Additionally or alternatively, the statistic(s) can include a rolling mean value. Additionally or alternatively, the statistic(s) can include a statistical model, such as a regression analysis, of the data measurements. Additionally or alternatively, a trained machine-learning model can be used to predict the force calibration offset for a subsequent time period using data from the current and/or prior time periods.

In some embodiments, the force calibration offset is determined using only the data measurements that were obtained while the user made a ski turn. In some embodiments, the force calibration offset is determined using only the data measurements that were obtained during the time period before the start of the ski turn. In some embodiments, the force calibration offset is determined using the data measurements that were obtained while the user made the ski turn and the time period before the start of the ski turn.

(c) Store the force calibration offset for the respective force sensor.

During processing of data measurements obtained during and/or after recalibration, the force calibration offset for the respective force sensor is subtracted from (or added to) each data measurement obtained from the respective force sensor. In one example, the data measurements obtained while the user made a ski turn and/or the data measurements obtained in the time period before the start of the ski turn can be processed using the newly stored force calibration offset. In another example, the data measurements obtained in a time period after the user made the ski turn can be processed using the newly stored force calibration offset, for example in the processing of data obtained during the next ski turn.

In some embodiments, before step (c) (storing the force calibration offset for the respective force sensor), each determined force calibration offset is compared to a maximum-allowable force sensor offset. The maximum-allowable force sensor offset can be an absolute number or a relative number. For example, using a relative number, the maximum-allowable force sensor offset can within a range of about −100% to +100% of the current/initial force calibration offset, including −50% to +50% of the current/initial force calibration offset, and −25% to +25% of the current/initial force calibration offset. If the determined force calibration offset is greater than the maximum-allowable force sensor offset, the determined force calibration offset is not stored as the force calibration offset. If the determined force calibration offset is lower than or equal to the maximum-allowable force sensor offset, the determined force calibration offset is stored as the force calibration offset. In some embodiments, if the minimum data measurement is greater than the maximum-allowable force sensor offset, rather than discarding the minimum data measurement, the force calibration offset is capped to equal the maximum-allowable force sensor offset.

In some embodiments, steps (a)-(c) can occur repeatedly in a loop. The loop can repeat immediately or after a delay, such as on a periodic basis or another time basis.

In some embodiments, the sensor data can be processed to remove noise before step (b). For example, outliers can be removed using an outlier detection and removal algorithm (for example, by comparing each value to a rolling mean), or the data first smoothed (for example, by taking the rolling median). Other denoising, outlier removal, and/or smoothing algorithms can be used.

In another example, the force sensors can be recalibrated using a rolling window. The rolling window can be or include a rolling time window. The rolling time window can have the same length (time duration) as the force recalibration period or a different time duration. In an example, the rolling time window resets with the start time set to the time when a new minimum data measurement occurred when either (1) a new minimum data measurement is detected for the respective sensor or (2) the rolling time window reaches a maximum length, whichever occurs first.

In other embodiments, the rolling window can be or include a rolling ski-turn window. In an example, the rolling ski-turn window resets when either (1) a new minimum data measurement is detected for the respective sensor or (2) the rolling ski-turn window reaches a maximum number of ski turns, whichever occurs first. The maximum number of ski turns can range from 2 turns to 20 turns. The maximum number of ski turns can be limited to ski turns within the same ski run. Alternatively, the maximum number of ski turns can include ski turns from sequential ski runs.

In other embodiments, the rolling window can be or include a combination of time and ski turns. In an example, the rolling ski-turn window resets when either (1) a new minimum data measurement is detected for the respective sensor, (2) the rolling ski-turn window reaches a maximum number of ski turns, or (3) the rolling window reaches a maximum length of time, whichever occurs first.

The recalibration of the force sensors using a rolling time window can include the following steps:

For each force sensor in each insole:

1. Perform steps (a)-(c), discussed above, for the initial calibration/recalibration of the force sensor. Additionally or alternatively, perform the motion and force sensor recalibration discussed above with respect to FIG. 21 for the initial calibration of the force sensor.

2. After the force sensor is calibrated (or recalibrated) and while the user has his/her feet on the insoles, obtain a data measurement at a predetermined sampling rate from the force sensor for up to the maximum length of the rolling time window. Store the time of the first data measurement as the start time of the rolling time window.

3. If the new data measurement is deemed to be an outlier, discard it and return to step 2. An outlier can be detected by using an outlier detection algorithm (for example, by comparing each value to a rolling mean). Other denoising, outlier removal, and/or smoothing algorithms can be used.

4. Compare the data measurement to the stored force calibration offset for the force sensor.

5. If the data measurement is lower than or equal to the stored force calibration offset for the force sensor (e.g., a new minimum data measurement is detected), store the data measurement as a new stored force calibration offset for the force sensor (e.g., replace the stored force calibration offset with the new minimum data measurement). Next, return to step 2 and reset the start time of the rolling time window to the current time.

6. If the respective data measurement is greater than the stored force calibration offset for the force sensor, determine the length of time that has passed (e.g., elapsed time) since the start time of the rolling time window. The elapsed time can be determined by subtracting the start time from the current time.

7. If the elapsed time is less than the maximum length of the rolling time window, return to step 2. The start time of the rolling time window is not reset when the elapsed time is less than the maximum length of the rolling time window.

8. If the elapsed time is greater than or equal to the maximum length of the rolling time window, determine the force calibration offset using the data measurements from the current time window (i.e., over the current rolling time window which is at its maximum length). The force calibration offset can be determined by finding the minimum data measurement for the force sensor over the rolling time window and the most recent time at which this occurred.

The force calibration offset determined for the current time window is then stored as a new stored force calibration offset for the force sensor (e.g., replace the stored force calibration offset with the new force calibration offset). Next, return to step 2 and reset the start time of the rolling time window. The start time of the rolling time window is reset to equal the time at which the most recent minimum was recorded.

Consider a sensor having a minimum value of +1 at between time=0 seconds and time=30 seconds where data measurements are sampled at a rate of 1 Hz and the maximum length of the rolling time window is 30 seconds. At time=30 seconds, the minimum value (+1) is stored as the initial force calibration offset, following steps (a)-(c). At the start of the second rolling time window at time=31 seconds, the next data measurement is +3, which is greater than the stored initial force calibration offset. Since the elapsed time of the second rolling time window is 0 seconds, additional data measurements are collected. At time=32 seconds, the next data measurement is +1, which is equal to the stored initial force calibration offset. This value of +1 is used as the new force calibration offset and the rolling time window is reset (e.g., to time=32 seconds). Alternatively, the value of +1 can be ignored (since it is equal to the stored initial force calibration offset), and the rolling time window is reset (e.g., to time=32 seconds).

At the start of the third rolling time window at time=33 seconds, the next data measurement is +4. From time=33 seconds to time=62 seconds, the data measurements are all higher than the stored force calibration offset (+1). At time=62 seconds, the elapsed time equals the maximum length of the rolling time window. The minimum data measurement over the third rolling time window is +2. This minimum value is now stored as the force calibration offset alongside the time at which it occurred. The start time of the fourth rolling time window is set to equal the time at which the most recent minimum was recorded in the third rolling time window.

In some embodiments, before storing the minimum data measurement as a new stored force calibration offset, the minimum data measurement can be compared to a maximum-allowable force sensor offset. The maximum-allowable force sensor offset can be an absolute number or a relative number. For example, using a relative number, the maximum-allowable force sensor offset can be within a range of about −100% to +100% of the current/initial force calibration offset, including −50% to +50% of the current/initial force calibration offset, and −25% to +25% of the current/initial force calibration offset. If the minimum data measurement is greater than the maximum-allowable force sensor offset, the minimum data measurement is not stored as the force calibration offset. If the minimum data measurement is lower than or equal to the maximum-allowable force sensor offset, the minimum data measurement is stored as the force calibration offset. In some embodiments, if the minimum data measurement is greater than the maximum-allowable force sensor offset, rather than discarding the minimum data measurement, the force calibration offset is capped to equal the maximum-allowable force sensor offset.

In some embodiments, the force calibration offset is not updated or replaced until the skier completes a turn to avoid a mid-turn change in the force calibration offset. The system can determine if the skier is making a turn using the motion sensors and/or the force sensors. In one example, the force calibration offsets for the force sensors in both insoles are not updated or replaced until the skier completes the turn. In another example, the force calibration offsets for the force sensors that are in the insole for the downhill ski are not updated or replaced until the skier completes the turn while the force calibration offsets for the force sensors that are in the insole for the uphill ski can be updated or replaced.

What has been described above includes examples of aspects of the claimed subject matter. It is, of course, not possible to describe every conceivable combination of components or methodologies for purposes of describing the claimed subject matter, but one of ordinary skill in the art may recognize that many further combinations and permutations of the disclosed subject matter are possible. Accordingly, the disclosed subject matter is intended to embrace all such alterations, modifications and variations that fall within the spirit and scope of the appended claims. Furthermore, to the extent that the terms "includes", "has" or "having" are used in either the detailed description or the claims, such terms are intended to be inclusive in a manner similar to the term "comprising" as "comprising" is interpreted when employed as a transitional word in a claim.

It is understood that the specific order or hierarchy of steps in the processes disclosed is an example of exemplary approaches. Based upon design preferences, it is understood that the specific order or hierarchy of steps in the processes may be rearranged while remaining within the scope of the present disclosure. The accompanying method claims present elements of the various steps in a sample order, and are not meant to be limited to the specific order or hierarchy presented Those of skill in the art would understand that information and signals may be represented using any of a variety of different technologies and techniques. For example, data, instructions, commands, information, signals, symbols, etc. may be referenced throughout the above description by other means.

Those of skill would further appreciate that the various illustrative logical blocks, modules, and algorithmic steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The invention claimed is:

1. A method of calibration of a system designed for analysis of ground reaction forces of a user's feet, wherein the system comprises a left and right footwear each with a plurality of force sensors, the method comprising:
   (a) obtaining respective data measurements from each force sensor over a time period while the user's feet are in the left and right footwear, the time period including a predetermined ski-turn window that includes a predetermined number of ski turns;
   (b) determining a respective statistic of the respective data measurements for each force sensor over the time period; and
   (c) storing the respective statistic as a respective calibration offset for a respective force sensor.

2. The method of claim 1, further comprising:
   after the time period, obtaining respective subsequent data measurements from each force sensor; and
   determining respective resulting force measurements for each sensor by subtracting the respective calibration offset from the respective subsequent data measurements.

3. The method of claim 1, further comprising detecting when the user is skiing, wherein the respective statistic is based only on the respective data measurements that were obtained while the user was skiing.

4. The method of claim 1, further comprising performing steps (a)-(c) in response to a detection of a recalibration event.

5. The method of claim 4, wherein the recalibration event comprises a temperature change that is greater than a maximum temperature change since a last calibration, an elapsed time that is greater than a maximum time duration since the last calibration, a detection of the user beginning to ski, a detection that the user has completed one or more of the ski turns, and/or a receipt of a manual recalibration request.

6. The method of claim 5, wherein:
the recalibration event comprises the detection that the user has completed the one or more of the ski turns,
the method further comprises determining respective resulting force measurements within each of the one or more of the ski turns for each sensor by subtracting the respective calibration offset from the respective ski turn data measurements, the respective ski turn data measurements obtained during a respective ski turn.

7. The method of claim 6, wherein:
the time period that the respective data measurements are obtained in step (a) includes the one or more of the ski turns and a length of time before the one or more of the ski turns, and
the respective statistic determined in step (b) is of the respective data measurements that were obtained during the length of time before the one or more of the ski turns.

8. The method of claim 1, further comprising:
determining whether the user is performing one or more of the ski turns; and
when the user is performing the one or more of the ski turns, delaying the storing of the respective statistic as the respective calibration offset for the respective force sensor until the one or more of the ski turns is/are completed.

9. The method of claim 1, wherein the respective statistic comprises a minimum, a maximum, an average, a median, a percentile, and/or a statistical model of the respective data measurements.

10. A method of calibration of a system designed for analysis of ground reaction forces of a user's feet, wherein the system comprises a left and right footwear each with a plurality of force sensors, the method comprising:
(a) obtaining a respective data measurement from each force sensor while the user's feet are in the left and right footwear;
(b) comparing each data measurement to a respective calibration offset for a respective force sensor;
(c) when the respective data measurement is higher than the respective calibration offset, returning to step (a) to obtain another respective data measurement from the respective force sensor;
(d) when the respective data measurement is lower than or equal to the respective calibration offset, storing the respective data measurement as a respective updated calibration offset for the respective force sensor;
(e) storing a start time of a force-calibration time window; and
(f) when the respective data measurement is lower than or equal to the respective calibration offset:
storing the respective data measurement as the respective updated calibration offset;
resetting the start time of the force-calibration time window; and
returning to step (a) to obtain another respective data measurement from each force sensor.

11. The method of claim 10, further comprising:
(g) determining an elapsed time of the force-calibration time window;
(h) comparing the elapsed time to a maximum time window length;
(i) when (1) the elapsed time is less than the maximum time window length and (2) the respective data measurement is lower than or equal to the respective calibration offset:
storing the respective data measurement as the respective updated calibration offset;
resetting the start time of the force-calibration time window; and
returning to step (a) to obtain another respective data measurement from each force sensor;
(j) when (1) the elapsed time is less than the maximum time window length and (2) the respective data measurement is higher than the respective calibration offset, returning to step (a) to obtain another respective data measurement from each force sensor; and
(k) when the elapsed time is greater than or equal to the maximum time window length:
determining a respective minimum data measurement from the respective data measurements obtained during the force-calibration time window;
storing the respective minimum data measurement as the respective updated calibration offset;
storing the time at which the minimum data measurement occurred as the respective start time of the force-calibration time window; and
returning to step (a) to obtain another respective data measurement from each force sensor.

12. The method of claim 10, further comprising performing steps (a) and (b) and step (c) or (d) in response to a detection of a recalibration event.

13. The method of claim 12, wherein the recalibration event comprises a temperature change that is greater than a maximum temperature change since a last calibration, an elapsed time that is greater than a maximum time duration since the last calibration, a detection of the user beginning to ski, a detection that the user has completed a ski turn, and/or a receipt of a manual recalibration request.

14. The method of claim 10, wherein the force-calibration time window includes a predetermined ski-turn window that includes a predetermined number of ski turns.

15. A system designed for analysis of ground reaction forces of a user's feet, comprising:
a left and right insole each with a plurality of force sensors;
one or more insole radio transceivers in electrical communication with the force sensors of each insole; and
a mobile terminal comprising:
a mobile radio transceiver in electrical communication with the one or more insole radio transceivers;
a microprocessor electrically coupled to the mobile radio transceiver; and
non-transitory memory electrically coupled to the microprocessor, the non-transitory memory storing computer-readable instructions that, when executed by the microprocessor, cause the microprocessor to:
(a) obtain respective data measurements from each force sensor over a time period while the user's feet are in the left and right footwear;
(b) determine a respective statistic of the respective data measurements for each force sensor over the time period, wherein the respective statistic comprises a minimum, a maximum, an average, a median, or a percentile of the respective data measurements; and (c) store the respective statistic as a respective calibration offset for a respective force sensor, wherein the computer-readable instructions, when executed by the microprocessor, further cause the microprocessor to:

detect that the user has completed a ski turn, wherein the time period that the respective data measurements are obtained in step (a) includes the ski turn; and determine respective resulting force measurements within the ski turn for each sensor by subtracting the respective calibration offset from respective ski turn data measurements, the respective ski turn data measurements obtained during the ski turn.

16. The system of claim 15, wherein:

the time period that the respective data measurements are obtained in step (a) includes the ski turn and a length of time before the ski turn, and the respective statistic determined in step (b) is of the respective data measurements that were obtained during the length of time before the ski turn.

17. A system designed for analysis of ground reaction forces of a user's feet, comprising:

a left and right insole each with a plurality of force sensors;

one or more insole radio transceivers in electrical communication with the force sensors of each insole; and a mobile terminal comprising:

a mobile radio transceiver in electrical communication with the one or more insole radio transceivers;

a microprocessor electrically coupled to the mobile radio transceiver; and non-transitory memory electrically coupled to the microprocessor, the non-transitory memory storing computer-readable instructions that, when executed by the microprocessor, cause the microprocessor to:

(a) obtain a respective data measurement from each force sensor while the user's feet are in the left and right footwear;

(b) compare each data measurement to a respective calibration offset for a respective force sensor;

(c) when the respective data measurement is higher than the respective calibration offset, return to step (a) to obtain another respective data measurement from each force sensor; and (d) when the respective data measurement is lower than or equal to the respective calibration offset, store the respective data measurement as a respective updated calibration offset, wherein the computer-readable instructions, when executed by the microprocessor, further cause the microprocessor to:

(e) store a start time of a force-calibration time window; and (f) when the respective data measurement is lower than or equal to the respective calibration offset:

store the respective data measurement as the respective updated calibration offset;

reset the start time of the force-calibration time window; and return to step (a) to obtain another respective data measurement from each force sensor.

18. The system of claim 17, wherein the computer-readable instructions, when executed by the microprocessor, further cause the microprocessor to:

(g) determine an elapsed time of the force-calibration time window;

(h) compare the elapsed time to a maximum time window length;

(i) when (1) the elapsed time is less than the maximum time window length and (2) the respective data measurement is lower than or equal to the respective calibration offset:

store the respective data measurement as the respective updated calibration offset;

reset the start time of the force-calibration time window; and return to step (a) to obtain another respective data measurement from each force sensor;

(j) when (1) the elapsed time is less than the maximum time window length and (2) the respective data measurement is higher than the respective calibration offset, return to step (a) to obtain another respective data measurement from each force sensor;

(k) when the elapsed time is greater than or equal to the maximum time window length:

determine a respective minimum data measurement from the respective data measurements obtained during the force-calibration time window;

store the respective minimum data measurement as the respective updated calibration offset;

store the time at which the minimum data measurement occurred as the respective start time of the force-calibration time window; and return to step (a) to obtain another respective data measurement from each force sensor.

19. The system of claim 17, wherein the computer-readable instructions, when executed by the microprocessor, further cause the microprocessor to perform steps (a) and (b) and step (c) or (d) in response to a detection of a recalibration event.

20. The system of claim 19, wherein the recalibration event comprises a temperature change that is greater than a maximum temperature change since a last calibration, an elapsed time that is greater than a maximum time duration since the last calibration, a detection of the user beginning to ski, a detection that the user has completed a ski turn, and/or a receipt of a manual recalibration request.

21. The method of claim 17, wherein the force-calibration time window includes a predetermined ski-turn window that includes a predetermined number of ski turns.

* * * * *